US009200089B2

(12) United States Patent
Urban et al.

(10) Patent No.: US 9,200,089 B2
(45) Date of Patent: Dec. 1, 2015

(54) SELF-REPAIRING CYCLIC OXIDE-SUBSTITUTED CHITOSAN POLYURETHANE NETWORKS

(71) Applicant: The University of Southern Mississippi, Hattiesburg, MS (US)

(72) Inventors: Marek W. Urban, Clemson, SC (US); Biswajit Ghosh, Dublin, OH (US)

(73) Assignee: The University of Southern Mississippi, Hattiesburg, MS (US)

( * ) Notice: Subject to any disclaimer, the term of this patent is extended or adjusted under 35 U.S.C. 154(b) by 97 days.

(21) Appl. No.: 14/152,023

(22) Filed: Jan. 10, 2014

(65) Prior Publication Data

US 2014/0127420 A1 May 8, 2014

Related U.S. Application Data

(62) Division of application No. 12/722,994, filed on Mar. 12, 2010, now Pat. No. 8,658,786.

(60) Provisional application No. 61/170,861, filed on Apr. 20, 2009.

(51) Int. Cl.
| | |
|---|---|
| *C08B 37/06* | (2006.01) |
| *C08B 37/08* | (2006.01) |
| *C08B 37/10* | (2006.01) |
| *C08B 37/00* | (2006.01) |
| *A61K 31/738* | (2006.01) |
| *A61K 31/722* | (2006.01) |
| *A61K 31/727* | (2006.01) |
| *A61K 31/732* | (2006.01) |
| *C08G 18/40* | (2006.01) |
| *C08G 18/48* | (2006.01) |
| *C08G 18/64* | (2006.01) |
| *C08G 18/79* | (2006.01) |
| *C09D 175/04* | (2006.01) |

(52) U.S. Cl.
CPC ............. *C08B 37/003* (2013.01); *A61K 31/722* (2013.01); *A61K 31/727* (2013.01); *A61K 31/732* (2013.01); *A61K 31/738* (2013.01); *C08B 37/0045* (2013.01); *C08B 37/0075* (2013.01); *C08G 18/4081* (2013.01); *C08G 18/4833* (2013.01); *C08G 18/6484* (2013.01); *C08G 18/792* (2013.01); *C09D 175/04* (2013.01)

(58) Field of Classification Search
None
See application file for complete search history.

(56) References Cited

U.S. PATENT DOCUMENTS 8,425,541 B2 * 4/2013 Masters et al. ................ 606/158

OTHER PUBLICATIONS

El-ghayouri et al., "Conbining Covalent and Noncovlent Cross-Linking: A Novel Terpolymer for Two-Step Curing Applications" Macromolecules (2003) vol. 36 pp. 3955-3959.*
Fangkangwanwong et al., "Chitosan gel formation via the chitosan-epichlorohydrin adduct and its subsequent mineralization with hydroxyapatite" Polymer (2006) vol. 47 pp. 6438-6445.*

* cited by examiner

*Primary Examiner* — Eric Olson
(74) *Attorney, Agent, or Firm* — Butler Snow LLP

(57) ABSTRACT

Thermosetting polymeric compositions, such as polyurethane compositions, and related methods are provided. The invention relates to coating and polymer compositions and related methods derived from a biodegradable natural polysaccharide compound such as chitosan, pectin, heparin, and combinations thereof reacted to a cyclic oxide compound, such as an oxetane, oxolane or oxepane compound. The compositions and methods of the present invention exhibit self-repairing properties upon exposure to ultraviolet (UV) light. The compositions and methods of the present invention can be used in many coating applications, such as the transportation, packaging, fashion, and biomedical industries.

17 Claims, 15 Drawing Sheets

SELF-REPAIRING CYCLIC OXIDE-SUBSTITUTED CHITOSAN POLYURETHANE NETWORKS

CROSS-REFERENCES TO RELATED APPLICATIONS

This application is a divisional application of U.S. patent application Ser. No. 12/722,994, filed on Mar. 12, 2010 and now U.S. Pat. No. 8,658,786, which claims benefit of priority to U.S. Provisional Application Ser. No. 61/170,861, filed Apr. 20, 2009, which are hereby incorporated by reference herein in their entirety.

STATEMENT REGARDING FEDERALLY SPONSORED RESEARCH OR DEVELOPMENT

This invention was made with government support under National Science Foundation (NSF) Cooperative Agreement #DMR-0213883. The government may have certain rights in this invention.

FIELD OF THE INVENTION

The invention relates to coating and polymer compositions and related methods derived from a reaction product of a biodegradable natural polysaccharide, such as chitosan and a cyclic oxide, such as oxetane, oxolane or oxepane compound. More specifically, the invention relates to coating and polymer compositions and related methods that allow the coating compositions to self-repair damage by exposure to an ultraviolet (UV) source.

BACKGROUND OF THE INVENTION

Thermosetting polymers, such as polyurethanes, have many properties that qualify them as high performance polymeric materials, but there are still a few shortfalls. For example, polyurethanes still suffer from mechanical damage, such as when a hard or sharp object hits vehicle, it is likely that it will leave a scratch. To try to combat these types of mechanical damage to coatings, the automotive industry looks for coatings with high scratch resistance. Due to their hardness and elasticity polyurethanes exhibit good scratch resistance, but can still suffer from mechanical damage.

Mechanical damage occurs in all types of substrates. For example, to heal mechanical damages in plants, suberin, tannins, phenols, or nitric oxide are activated to prevent further lesions, whereas in a human skin outer flow of blood cells are arrested by the crosslink network of fibrin, giving rise to wound-healing. Concentration gradients or stratification in living organisms inspired the development of spatially heterogeneous remendable polymers, composites containing micro-encapsulated spheres, encapsulated fibers, reversible cross-linking, and microvascular networks.

Attempts have been made by others to repair mechanical damage to various substrates. One such example includes epoxy matrices containing a glass hollow fiber filled with a monomer and an initiator with the 'bleeding' ability to heal polymer networks during crack formation. Similar phenomenon was utilized in another approach, where a micro-encapsulated dicyclopentadiene monomer was introduced in a catalyst embedded polymer matrix, which healed the crack by the ring opening of the monomer. Reversibility of Diels-Alder reactions resulted in another attractive approach to thermally repair damaged areas which utilized malemide-furan adducts. Mimicking of microvascular structures, water-responsive expandable gels, and formation of supramolecular assemblies are other avenues of remendability.

While progress has been made in attempts to repair damage to various types of systems, coatings still lack the ability to repair mechanical damage to which they are exposed. A need exists for polymer systems that are capable of self-repairing mechanical damage to which they are exposed. It would be advantageous for the polymers to be useful in coatings, so that the coating could be able to mend itself. It would be further advantageous if the repair could occur when the coating is simply exposed to ambient conditions, such as UV exposure from the sun.

SUMMARY OF THE INVENTION

In view of the foregoing, thermosetting polymeric compositions and related methods are provided as embodiments of the present invention. Methods of making the compositions are provided. Methods of using the compositions are also provided. The thermosetting polymeric compositions and related methods enable substrates upon which the compositions are applied to self-repair mechanical damage upon exposure to ultraviolet (UV) sources, such as the sun.

For example, as an embodiment of the present invention, an oxetane-substituted chitosan polyurethane composition is provided. Oxetane generally refers to 1,3-propylene oxide. In this embodiment, the cyclic oxide-substituted chitosan polyurethane composition comprises:

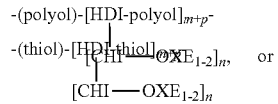

wherein HDI=an isocyanate, CHI=a chitosan compound, OXE=an oxetane, oxolane or oxepane compound, m=a number of moles of HDI used to produce the composition; p=a number of moles of a polyol used to produce the composition, and n=a number of moles of the chitosan compound used to produce the composition. In an aspect, m ranges from 3-450, p ranges from 0-540; and n ranges from 5-650.

As another embodiment of the present invention, an cyclic oxide-substituted chitosan composition is provided. In this embodiment, the cyclic oxide-substituted chitosan composition comprises:

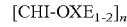

wherein OXE=oxetane, oxolane or oxepane, and n=a number of moles of a chitosan compound used to produce the composition. In an aspect, n ranges from 5-650. In an aspect, the OXE-substituted chitosan composition comprises:

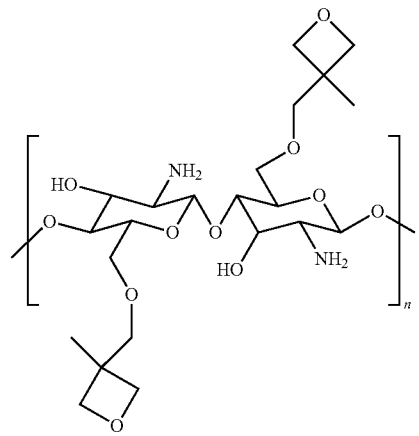

wherein n=a number of moles of the chitosan compound used to produce the composition. In an aspect, n ranges from 5-650. In this example, the oxetane is 3,3 dimethyloxetane.

Besides using chitosan, other biodegradable natural polysaccharides, such as pectin and heparin or combinations thereof. In an aspect, as an embodiment of the present invention, an oxetane-substituted biodegradable natural polysaccharide composition is provided. The composition comprises:

[BNP-OXE$_{1-2}$]$_n$ wherein BNP=a biodegradable natural polysaccharide compound selected from the group consisting of chitosan, pectin, heparin, and combinations thereof, OXE=an oxetane, oxolane or oxepane compound, and n=5-650. Other suitable types of biodegradable natural polysaccharide compounds that can be used in embodiments of the present invention will be apparent to those of skill in the art and are to be considered within the scope of the present invention.

Besides using oxetane, other substituted-cyclic oxide compounds can be used in embodiments of the present invention. For example, 1,6-hexylene oxide (i.e., oxepane) or 1,4-butylene oxide (i.e., oxolane or tetrahydrofuran) can be used. Other suitable types of substituted-ring compounds that can be used in embodiments of the present invention will be apparent to those of skill in the art and are to be considered within the scope of the present invention.

TABLE 1

| | Chemical Name | IUPAC | Commercial Name | Structure |
|---|---|---|---|---|
| Four Member | 1,3-propylene oxide | Oxetane | Oxetane | 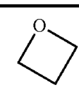 |
| Five Member | 1,4-butylene oxide | Oxolane | Tetrahydrofuran | 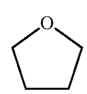 |
| Seven Member | 1,6-hexylene oxide | Oxepane | | 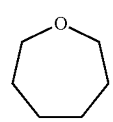 |

Besides the compositions, methods of making the compositions are also provided. For example, a method of producing a polyurethane composition capable of self-repairing mechanical damage to a substrate on which the composition has been applied is provided as an embodiment of the present invention. In this method of producing the polyurethane composition, a chitosan compound is contacted with a cyclic oxide such as an oxetane, oxolane or oxepane compound to produce a precursor product comprising:

[CHI-OXE$_{1-2}$]$_n$ wherein OXE=oxetane, oxolane or oxepane, and n=a number of moles of a chitosan compound used to produce the composition. In an aspect, n ranges from 5-650. The precursor product is then contacted with an isocyanate and a polyol to produce the polyurethane composition comprising:

-(polyol)-[HDI-polyol]$_{m+p}$-
|
[CHI——OXE$_{1-2}$]$_n$,    or

-(thiol)-[HDI-thiol]$_{m+p}$-
|
[CHI——OXE$_{1-2}$]$_n$ wherein HDI=an isocyanate, CHI=a chitosan compound, OXE=oxetane, oxolane or oxepane m=a number of moles of HDI used to produce the composition; p=a number of moles of a polyol used to produce the composition, and n=a number of moles of the chitosan compound used to produce the composition. In an aspect, m ranges from 3-450, p ranges from 0-540; and n ranges from 5-650. Representative OXE reactants include 3-ethyl-3-phenoxymethyloxetane, 3-ethyl-3-allyloxymethyloxetane, 3-methyl-3-phenoxymethyloxetane, 3-ethyl-3-[(2-ethylhexyloxy)methyl]oxetane, bis{[(1-ethyl (3-oxetanyl)]methyl}ether, 1,4-bis[(3-ethyl-3-oxetanyl-methoxy)methyl]benzene, bis[(3-ethyl-3-oxetanylmethoxy) methyl]terephthalate, bis[(3-ethyl-3-oxetanylmethoxy) methyl]phenyl ether, 2-phenyloxetane, 3,3 bischloromethyloxetane, 3,3-dimethyloxetane and 3,3-bis-bromomethyloxetane. Similarly substituted oxepane and oxolane compounds can also be used.

As another method embodiment of the present invention, a method of repairing mechanical damage to a substrate is provided. In this embodiment, a cyclic oxide-substituted chitosan polyurethane composition is applied to a substrate. One such oxetane-substituted chitosan polyurethane composition comprises:

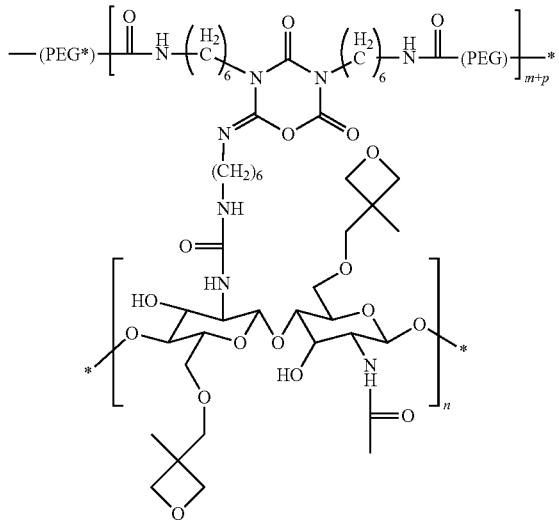

wherein PEG=a polyol or a thiol, m=a number of moles of an isocyanate used to produce the composition; p=a number of moles of the polyol used to produce the composition, and n=a number of moles of a chitosan compound used to produce the composition. In an aspect, m ranges from 3-450, p ranges from 0-540; and n ranges from 5-650. Once the composition is applied to the substrate, the substrate is exposed to a UV source to initiate self-repair of the mechanical damage to the substrate. The compositions described herein prophylactically repair mechanical damage to a substrate upon application of the compositions described herein. Upon exposure of the substrate to a UV source, the composition initiates self-repair of the mechanical damage to the substrate.

Figure 1:
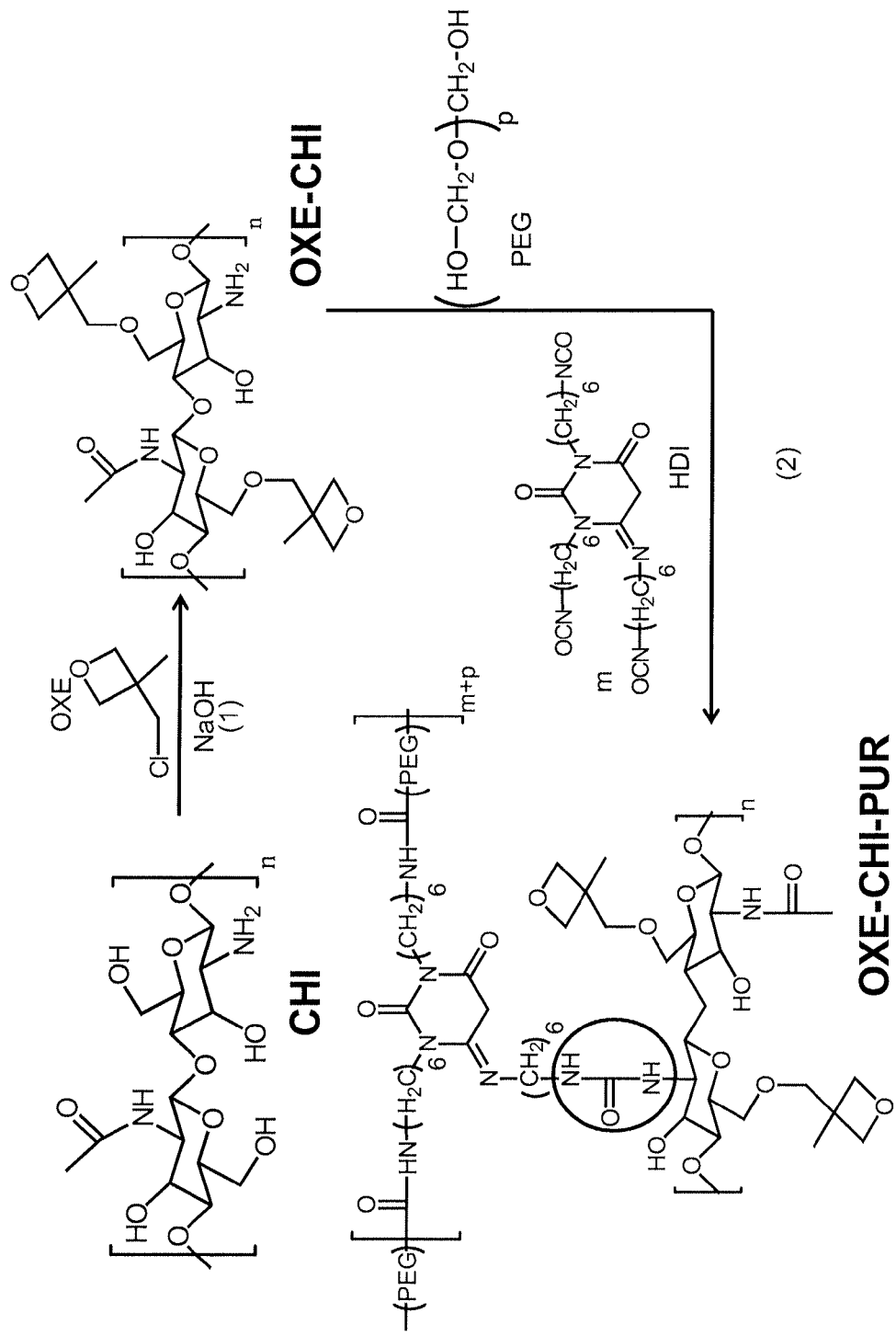
FIG. 1 is a schematic illustrating the synthesis steps involved in the formation of OXE-CHI illustrating the reactions of oxetane with CHI leading to the formation of OXE-CHI precursor and the reactions of OXE-CHI with HDI and PEG leading to formations of remendable OXE-CHI-PUR network in accordance with embodiments of the present invention.

While the invention is susceptible to various modifications and alternative forms, specific embodiments have been shown by way of example in the drawings and will be described in detail herein. However, it should be understood that the invention is not intended to be limited to the particular forms disclosed. Rather, the intention is to cover all modifications, equivalents and alternatives falling within the spirit and scope of the invention as defined by the appended claims.

DESCRIPTION OF ILLUSTRATIVE EMBODIMENTS

Illustrative embodiments of the invention are described below as they might be employed in the reactions and compositions related to thermosetting polymers. In the interest of clarity, not all features of an actual implementation are described in this specification. It will of course be appreciated that in the development of any such actual embodiment, numerous implementation-specific decisions must be made to achieve the developers' specific goals, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description.

Thermosetting polymeric compositions, such as polyurethane compositions, and related methods are provided as embodiments of the present invention. Methods of making the compositions are provided, Methods of using the compositions are also provided.

More specifically, polyurethane networks are provided as embodiments of the present invention that exhibit self-repairing properties upon exposure to ultraviolet (UV) light. The polyurethane network includes a cyclic oxide such as oxetane, oxolane or oxepane-substituted chitosan precursor incorporated into a two-component polyurethane. Upon mechanical damage of the network, oxide rings (e.g. oxetane, oxolane or oxepane rings) open to create two reactive ends. When exposed to UV light, chitosan chain scission occurs that forms crosslinks with the reactive oxide ends, thus repairing the network. The produced materials are capable of repairing themselves in less than an hour and can be used in many coatings applications ranging from transportation to packaging or fashion and biomedical industries. The methods and compositions made in accordance with embodiments of the present invention can also be used in various other industries, as will be apparent to those of skill in the art and are to be considered within the scope of the present invention.

In embodiments of the present invention, heterogeneous polyurethane (PUR) networks are produced based on cyclic oxide-substituted derivative of chitosan (OXE-CHI) being reacted with hexamethylene diisocyanate (HDI) and polyethylene glycol (PEG) to form heterogeneous OXE-CHI-PUR networks. Each of the components used to produce the polyurethane networks in the present invention possess specification properties that serve specific functions. For example, PUR networks generally provide desirable heterogeneity through polyurethane and polyurea components and OXE- CHI provides the cleavage of a constrained 4, 5 or 7-membered ring (OXE) and UV sensitivity through CHI. Chitosan is generally a product of deacetylation of chitin, which is the structural element of exoskeletons of crustaceans (crabs, shrimp, etc.) that occurs in abundance in nature.

For example, as an embodiment of the present invention, a cyclic oxide-substituted chitosan polyurethane (OXE-CHI-PUR) composition is provided. In this embodiment, the oxetane-substituted chitosan polyurethane composition comprises:

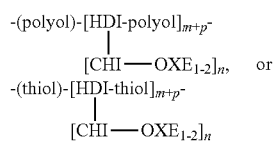

wherein HDI=an isocyanate, CHI=a chitosan compound, OXE=an oxetane, oxolane or oxepane compound, m=a number of moles of HDI used to produce the composition; p=a number of moles of a polyol used to produce the composition, and n=a number of moles of the chitosan compound used to produce the composition. In an aspect, m ranges from 3-450, p ranges from 0-540; and n ranges from 5-650. Representative OXE reactants include 3-ethyl-3-phenoxymethyloxetane, 3-ethyl-3-allyloxymethyl oxetane, 3-methyl-3-phenoxymethyloxetane, 3-ethyl -3-[(2-ethylhexyloxy)methyl]oxetane, bis{[(1-ethyl (3-oxetanyl)]methyl}ether, 1,4-bis[(3-ethyl -3-oxetanylmethoxy)methyl]benzene, 3,3-dimethyl oxetane, bis[(3-ethyl -3-oxetanylmethoxy)methyl]terephthalate, bis[(3-ethyl-3-oxetanylmethoxy)methyl]phenyl ether, 2-phenyloxetane, 3,3-bischloromethyloxetane, and 3,3-bis-bromomethyloxetane. Similarly substituted oxepane and oxolane compounds can also be used.

The types of isocyanates used in embodiments of the present invention can be varied. For example, in an aspect, the isocyanate can include methylenediisocyanate (MDI); hexamethylenediisocyanate (HDI); isophorenediisocyanate (IPDI); toluenediisocyanate (TDI); 2,4-toluene diisocyanate; 2,6-toluene diisocyanate; 2,2'-methylenediphenylene diisocyanate; 2,4'-methylenediphenylene diisocyanate; 4,4'-methylenediphenylene diisocyanate; polyphenylene polymethylene polyisocyanate; saturated 2,4-methylcyclohexane diisocyanate, saturated 2,6-methylcyclohexane diisocyanate; 2,2'-methylene dicyclohexylene diisocyanate; 2,4'-methylene dicyclohexylene diisocyanate; 4,4'-methylene dicyclohexylene diisocyanate; isophorone diisocyanate; 1,4-diisocyanatobutane; 1,5-diisocyanatopentane; 1,6-diisocyanatohexane; 1,4-cyclohexane diisocyanate; isomeric mixtures thereof; or combinations thereof. Other suitable types of isocyanates will be apparent to those of skill in the art and are to be considered within the scope of the present invention.

Besides varying the types of isocyanates used in compositions and methods described herein, the types of polyols used can also be varied. In an aspect, for example, the polyol can include ethylene glycol, diethylene glycol, triethylene glycol, tetraethylene glycol, polyethylene glycol, propylene glycol, dipropylene glycol, polypropylene glycol, 1,4-butanediol, 1,6-hexanediol, polytetramethylene glycol, polyesterdiol, derivatives thereof, or combinations thereof, and mixtures thereof. Other suitable types of polyols will be apparent to those of skill in the art and are to be considered within the scope of the present invention.

Similarly, in embodiments of the present invention that use thiols, the types of thiols used can be varied. For example, the thiol can include polythiol, pentaerythritol tetrakis(3-mercaptoproprionate) (PET3MP), trifunctional thiols, tetrafunctional thiols, thiol esters, thiol acrylates, or combinations thereof. Other suitable types of thiols will be apparent to those of skill in the art and are to be considered within the scope of the present invention.

In an aspect, the composition comprises a structure as follows:

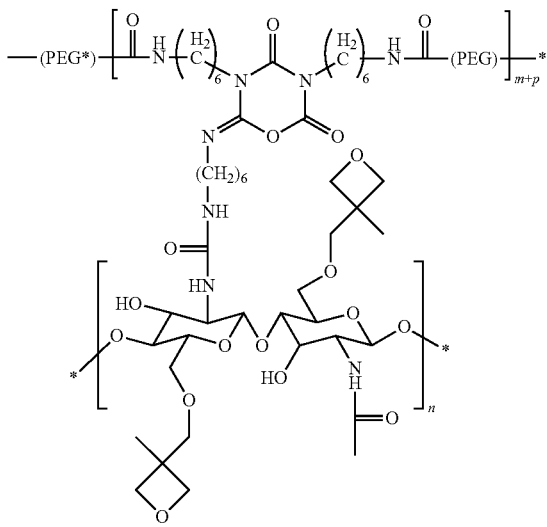

wherein PEG=a polyol, m=a number of moles of an isocyanate used to produce the composition; p=a number of moles of the polyol used to produce the composition, and n=a number of moles of a chitosan compound used to produce the composition. In an aspect, m ranges from 3-450, p ranges from 0-540; and n ranges from 5-650.

The compositions described herein are useful in a variety of application. For example, the compositions described herein can be used in various types of coatings. The coatings can include the compositions described herein. In an aspect, the coatings can include the cyclic oxide-substituted chitosan polyurethane (OXE-CHI-PUR) composition having a formula as follows:

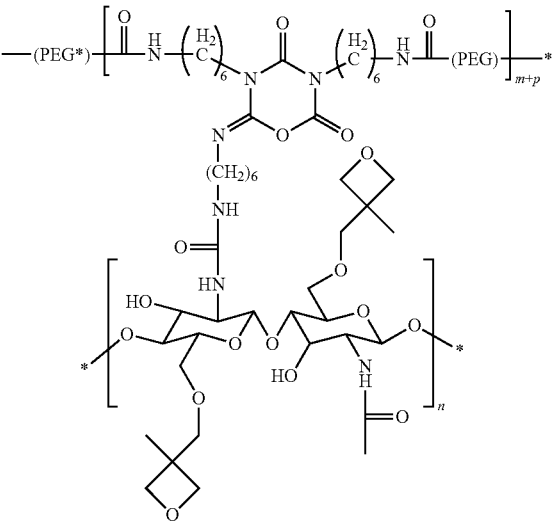

wherein PEG=polyethylene glycol, m=a number of moles of an isocyanate used to produce the composition; p=a number of moles of the polyol used to produce the composition, and n=a number of moles of a chitosan compound used to produce the composition. In an aspect, m ranges from 3-450, p ranges from 0-540; and n ranges from 5-650.

As another embodiment of the present invention, an oxetane-substituted chitosan composition is provided. In this embodiment, the oxetane-substituted chitosan (OXE-CHI) composition comprises:

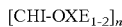
[CHI-OXE$_{1-2}$]$_n$ wherein OXE=oxetane, oxolane or oxepane, and n=a number of moles of a chitosan compound used to produce the composition. In an aspect, the oxetane-substituted chitosan composition comprises:

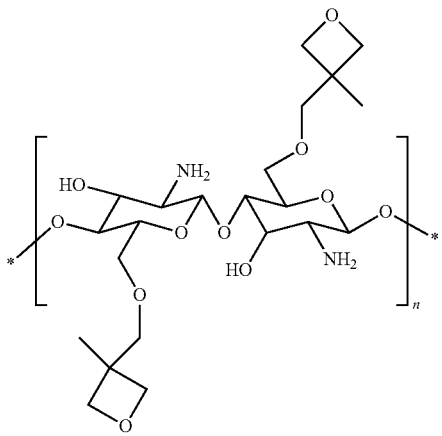

wherein n=a number of moles of the chitosan compound used to produce the composition. In an aspect, n ranges from 5-650.

Besides using chitosan, other biodegradable natural polysaccharides, such as pectin and heparin or combinations thereof. In an aspect, as an embodiment of the present invention, an oxetane-substituted biodegradable natural polysaccharide composition is provided. The composition comprises:

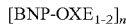
[BNP-OXE$_{1-2}$]$_n$ wherein BNP=a biodegradable natural polysaccharide compound selected from the group consisting of chitosan, pectin, heparin, and combinations thereof, OXE=an oxetane, oxolane or oxepane compound, and n=5-650. In an aspect, oxetane-substituted biodegradable natural polysaccharide composition can be reacted with a polyol and an isocyanate to produce an oxetane-substituted biodegradable natural polysaccharide polyurethane composition. Other suitable types of biodegradable natural polysaccharide compounds that can be used in embodiments of the present invention will be apparent to those of skill in the art and are to be considered within the scope of the present invention.

Besides using oxetane, other substituted-ring compounds can be used in embodiments of the present invention. For example, 1,6-hexylene oxide (i.e., oxepane) or 1,4 butylene oxide (i.e., oxolane or tetrahydrofuran) can be used. Other suitable substituted-ring compounds that can be used in embodiments of the present invention will be apparent to those of skill in the art and are to be considered within the scope of the present invention.

Besides the compositions, methods of making the compositions are also provided as embodiments of the present invention. For example, a method of producing a polyurethane composition capable of self-repairing mechanical damage to a substrate on which the composition has been applied is provided as an embodiment of the present invention. In this method of producing the polyurethane composition, a chitosan compound is contacted with an oxetane compound to produce a precursor product comprising:

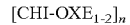
[CHI-OXE$_{1-2}$]$_n$ wherein OXE=oxetane, oxolane or oxepane, and n=a number of moles of a chitosan compound used to produce the composition. In an aspect, n ranges from 5-650. The precursor product is then contacted with an isocyanate and a polyol to produce the polyurethane composition comprising:

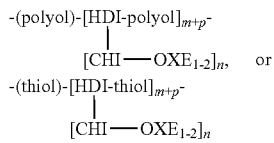

wherein HDI=an isocyanate, CHI=a chitosan compound, OXE=an oxetane, oxolane or oxepane compound, m=a number of moles of HDI used to produce the composition; p=a number of moles of a polyol used to produce the composition, and n=a number of moles of the chitosan compound used to produce the composition. In an aspect, m ranges from 3-450, p ranges from 0-540; and n ranges from 5-650.

In an aspect of the methods described herein, when the chitosan compound contacts the oxetane compound, the step typically occurs in the presence of a solvent. Any basic solvent that is compatible with the components used in the methods and compositions described herein can be used, as will be understood by those of skill in the art. In an aspect, the solvent can be sodium hydroxide, sodium carbonate, potassium hydroxide, or combinations thereof. Other suitable types of solvents that can be used in embodiments of the present invention will be apparent to those of skill in the art and are to be considered within the scope of the present invention.

As another method embodiment of the present invention, a method of repairing mechanical damage to a substrate is provided. In this embodiment, a cyclic oxide-substituted chitosan polyurethane composition is applied to a substrate. The oxetane-substituted chitosan polyurethane composition comprises:

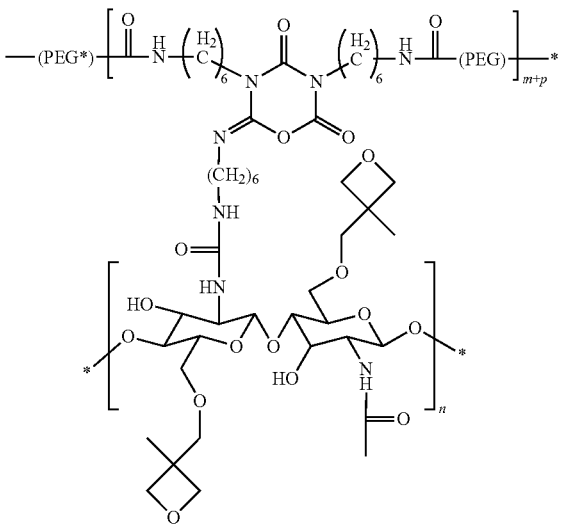

wherein PEG=a polyol or a thiol, m=a number of moles of an isocyanate used to produce the composition; p=a number of moles of the polyol used to produce the composition, and n=a number of moles of a chitosan compound used to produce the composition. In an aspect, m ranges from 3-450, p ranges from 0-540; and n ranges from 5-650. Once the composition is applied to the substrate, the substrate is exposed to a UV source to initiate self-repair of the mechanical damage to the substrate. The compositions described herein prophylactically repair mechanical damage to a substrate upon application of the compositions described herein. Upon exposure of the substrate to a UV source, the composition initiates self-repair of the mechanical damage to the substrate.

In embodiments using chitosan, the chitosan can have a degree of deacetylation ranging from about 75% to about 85%. Chitosan have other degrees of deacetylation can be used, as will be understood by those of skill in the art.

The oxetane compound can be supplied using various types of oxetane compounds. For example, the oxetane compound can be a halide-substituted oxetane compound comprising 3-(Chloromethyl)-3-methyloxetane, methyl-substituted oxetane, or combinations thereof. Other suitable types of oxetane compounds that can be used in the present invention will be apparent to those of skill in the art and are to be considered within the scope of the present invention. Representative OXE reactants include 3-ethyl-3-phenoxymethyl oxetane, 3-ethyl-3-allyloxymethyloxetane, 3-methyl-3-phenoxymethyloxetane, 3-ethyl-3-[(2-ethylhexyloxy)methyl]oxetane, bis{[(1-ethyl(3-oxetanyl)]methyl}ether, 1,4-bis[(3-ethyl-3-oxetanylmethoxy)methyl]benzene, 3,3-dimethyloxetane, bis[(3-ethyl-3-oxetanylmethoxy)methyl] terephthalate, bis[(3-ethyl-3-oxetanylmethoxy)methyl] phenyl ether, 2-phenyloxetane, 3,3-bischloromethyloxetane, and 3,3-bisbromomethyloxetane. Similarly substituted oxepane and oxolane compounds can also be used.

The compositions and methods described herein can be used in many types of applications. The types of substrates on which the compositions can be applied thereto can include metal, plastic, glass, or combinations thereof. More specifically, the types of substrates on which the compositions can be applied thereto can include motor crafts, automobiles, mechanical parts, weapons, military equipment, watercrafts, jewelry, electronics, or combinations thereof. The compositions and methods described herein can be used in other applications, such as on different substrates, as will be apparent to those of skill in the art and are to be considered within the scope of the present invention.

Figure 4:
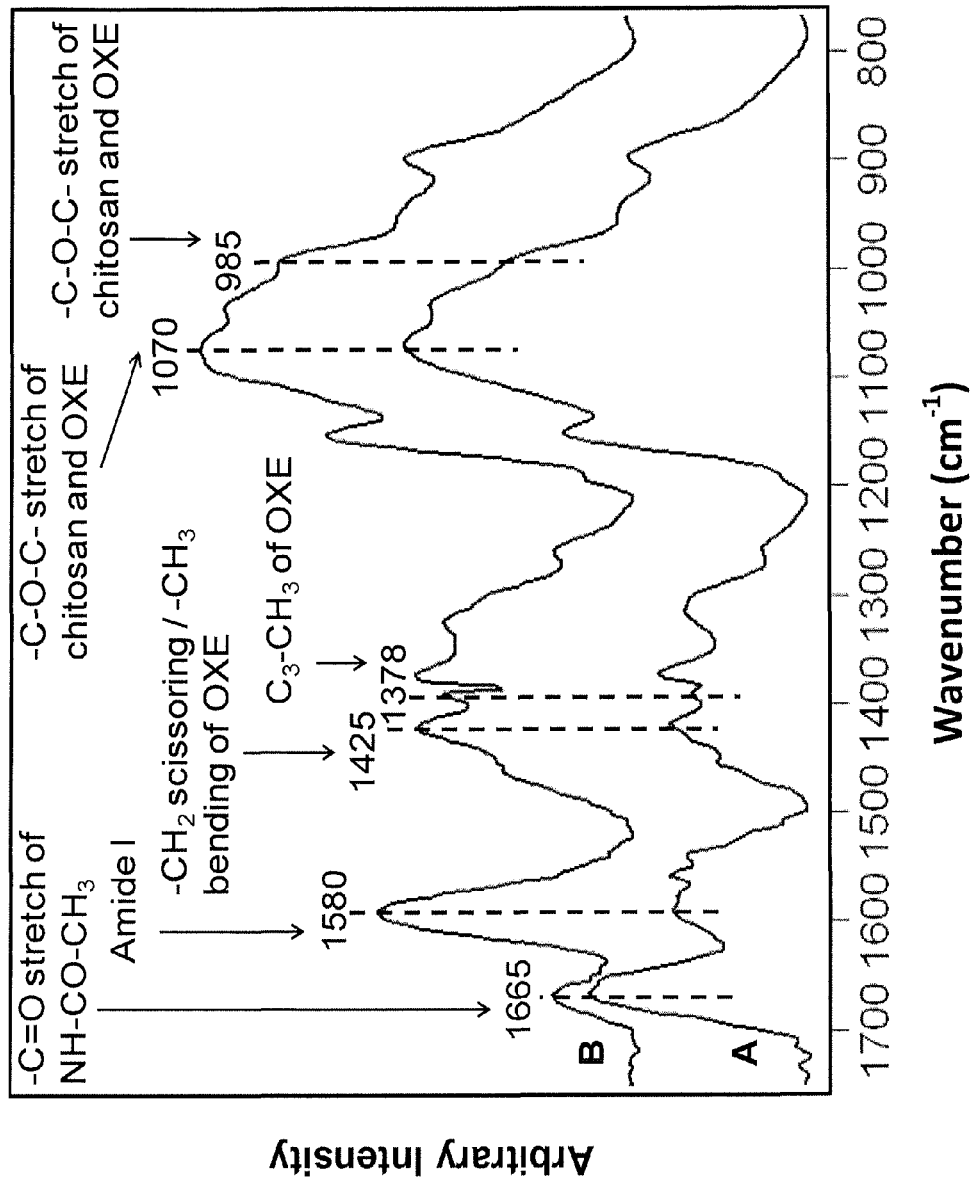
FIG. 4 illustrates an ATR FT-IR spectra of (A) CHI and (B) OXE-CHI products made in accordance with embodiments (wherein OXE is oxetane) of the present invention.
Figure 5:
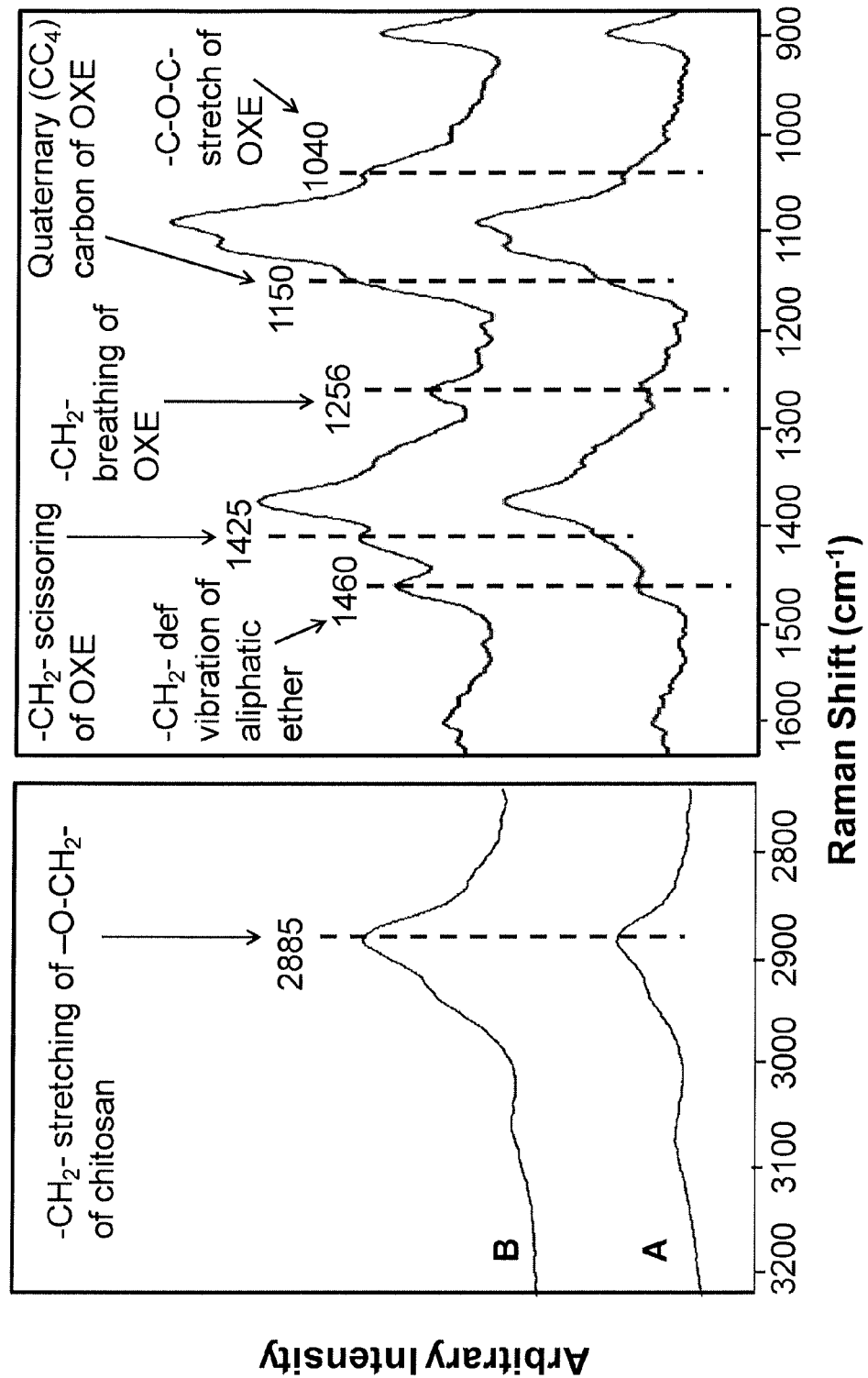
FIG. 5 illustrates a Raman spectra of (A) CHI and (B) OXE-CHI products made in accordance with embodiments (wherein OXE is oxetane) of the present invention.
Figure 6:
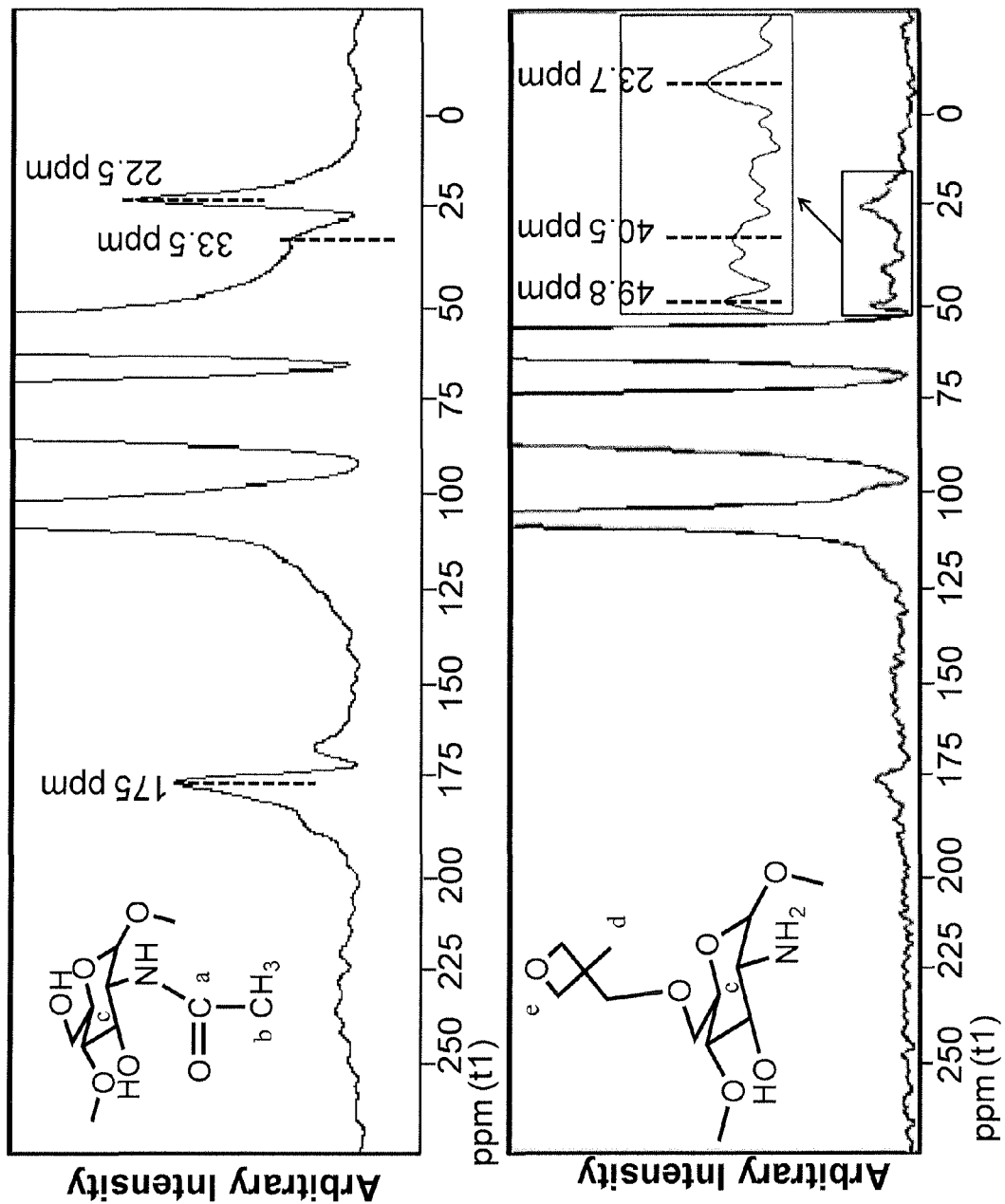
FIG. 6 illustrates a solid state $^{13}$C NMR spectra of (A) CHI and (B) OXE-CHI products in accordance with embodiments (wherein OXE is oxetane) of the present invention.

Turning to the Figures, FIG. 1 illustrates a two-step reaction sequence leading to the OXE-CHI-PUR formation. In the first reaction step that is used for the synthesis of OXE-CHI, the primary alcohol of CHI is reacted with chloromethyl of oxetane, OXE. An OXE ring is reacted to the $C_6$ position of the chitosan molecule, which is confirmed by IR, Raman and $^{13}$C-NMR spectroscopy as shown in FIGS. 4, 5, and 6, respectively.

Figure 7:
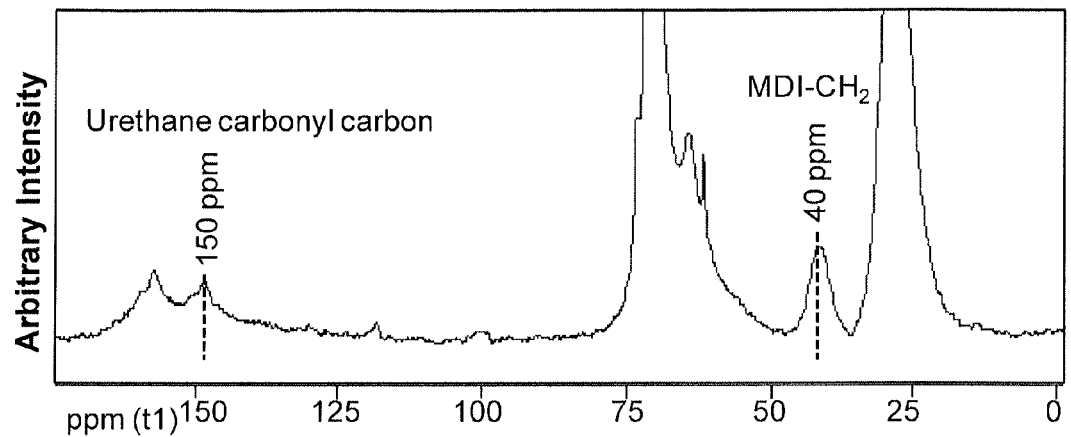
FIG. 7 illustrates a solid state $^{13}$C NMR spectra of PUR network in accordance with embodiments of the present invention.
Figure 8:
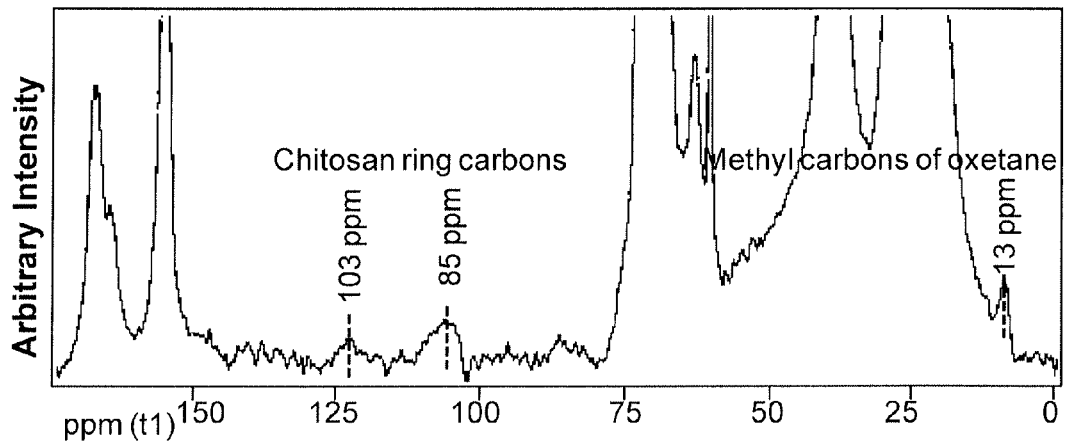
FIG. 8 illustrates a solid state $^{13}$C NMR spectra of OXE-CHI-PUR network in accordance with embodiments (wherein OXE is oxetane) of the present invention.

The second reaction step illustrates the reactions leading to the incorporation of oxetane OXE-CHI into the tri-functional HDI in the presence of PEG (1:1.4 and 1:1.33 molar ratios), which can be confirmed by IR and $^{13}$C-NMR spectroscopy as shown in FIGS. 7 and 8, respectively.

Figure 2:
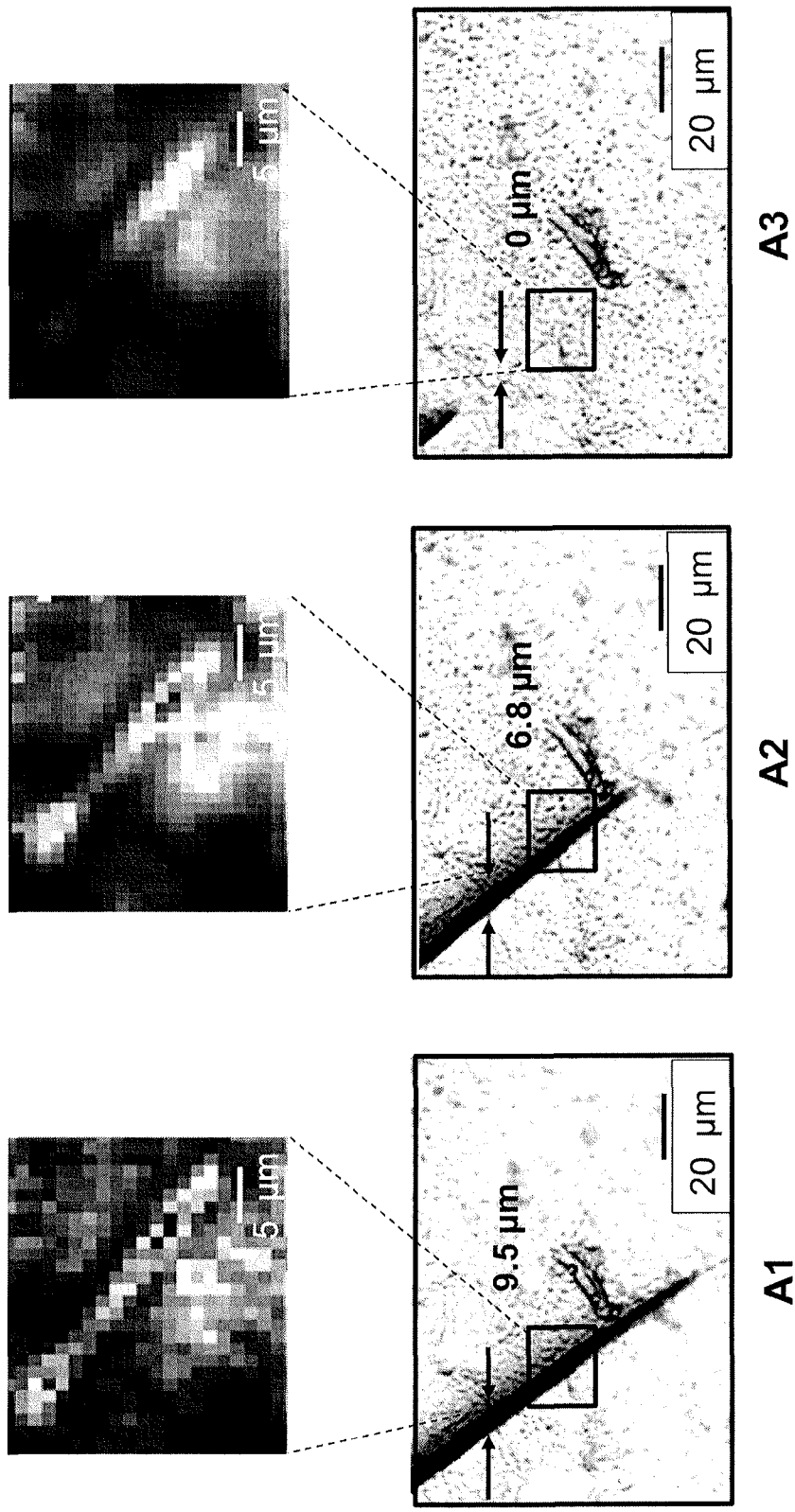
FIG. 2 represents IR (upper) images and optical (lower) images of OXE-CHI-PUR networks (wherein OXE is oxetane) recorded as a UV exposure time, with A1 representing 0 min; A2 representing 15 min; and A3 representing 30 min in accordance with embodiments of the present invention.

To demonstrate the self-healing properties of the compositions described herein, networks were allowed to crosslink under ambient conditions to form solid films, which were then mechanically damaged by creating a scratch. FIG. 2, A1 illustrates a mechanical damage to oxetane OXE-CHI-PUR films. When the damaged area is exposed to a 120 W fluorescent UV lamp at 302 nm wavelength of light for 15 min. (FIG. 2, A2) and 30 min (FIG. 2, A3), the damaged area vanishes.

A series of controlled experiments were conducted on specimens prepared by varying the molar ratios of oxetane OXE-CHI with respect to the PUR content, as shown in Table S1. Optical images shown in FIG. 3, A-D, illustrate the results of the experiments conducted under the same UV exposure conditions (at 0, 15, and 30 min) conducted on the specimens listed in Table S1.

TABLE S1

| Specimen | Molar Ratios of Individual Components | Exposure Time (min) | | |
|---|---|---|---|---|
| | | 0 | 15 | 30 |
| | | Damage Width (μm) + 0.1 | | |
| A | PUR HDI:PEG:CHI = 1:1.5:0 | 10 | 10 | 10 |
| B | CHI-PUR MI:PEG:CHI = 1:1.4:0.57 × $10^{-4}$ | 20.5 | 20.5 | 20.5 |
| C | OXE-CHI-PUR HDI:PEG:OXE-CHI = 1:1.4:0.57 × $10^{-4}$ | 2.26 | 1.08 | 0 |
| D | OXE-CHI-PUR HDI:PEG:OXE-CHI = 1:1.33:1.17 × $10^{-4}$ | 6 | 5.2 | 0 |

Figure 3:
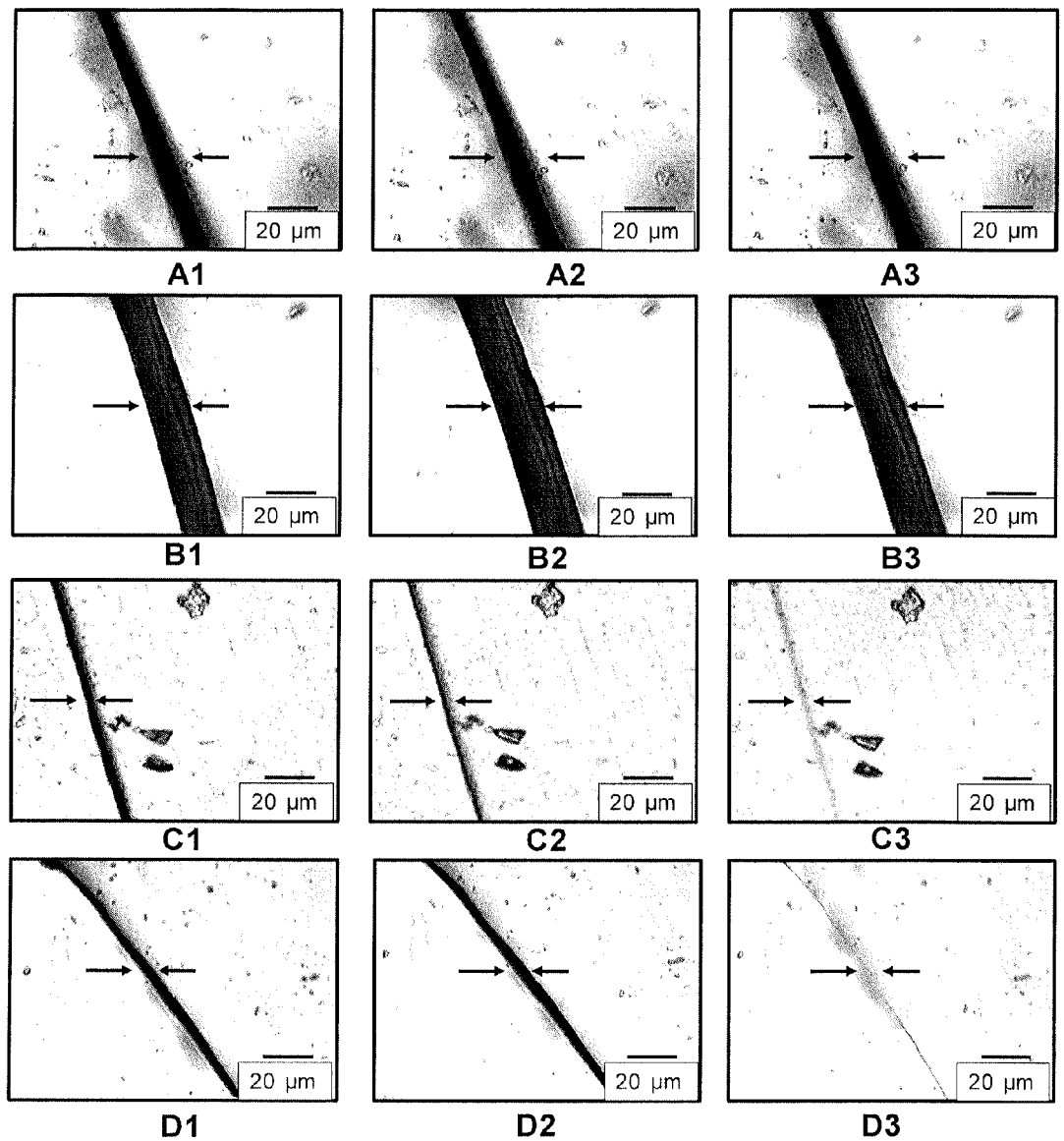
FIG. 3 represents optical images of mechanically damaged films of: PUR (A1, A2, and A3 are images after exposure for 0, 15 and 30 min to UV radiation; HDI/PEG/CHI=1:1.5:0); CHI-PUR (B1, B2, and B3 are images after exposure for 0, 15 and 30 min to UV radiation; HDI/PEG/CHI=1:1.4:0.57× $10^{-4}$); OXE-CHI-PUR (C1, C2, and C3 are images after exposure for 0, 15 and 30 min to UV radiation; HDI/PEG/OXE-CHI=1:1.4:0.57×$10^{-4}$); OXE-CHI-PUR (D1, D2 and D3 are images after exposure for 0, 15 and 30 min to UV radiation; HDI/PEG/OXE-CHI=1:1.33:1.17×$10^{-4}$) made in accordance with embodiments (wherein OXE is oxetane) of the present invention.

The experiments illustrate that the presence of oxetane OXE-CHI component is an important factor in the remendability of the network, as shown in FIGS. 2 and 3. As can be seen in Table S1, when using only PUR or CHI-PUR (Specimens A and B in Table S1), neither of these specimens are able to repair the mechanical damage. In contrast, the presence of the covalently bonded OXE-CHI components (Specimens C and D in Table S1) facilitates the self-healing process. Table Si also shows the damage width as a function of UV exposure evaluations conducted on the specimens shown in FIG. 3. Note that the rate of repair for networks containing half the OXE-CHI precursor concentration is also reduced.

Figure 9:
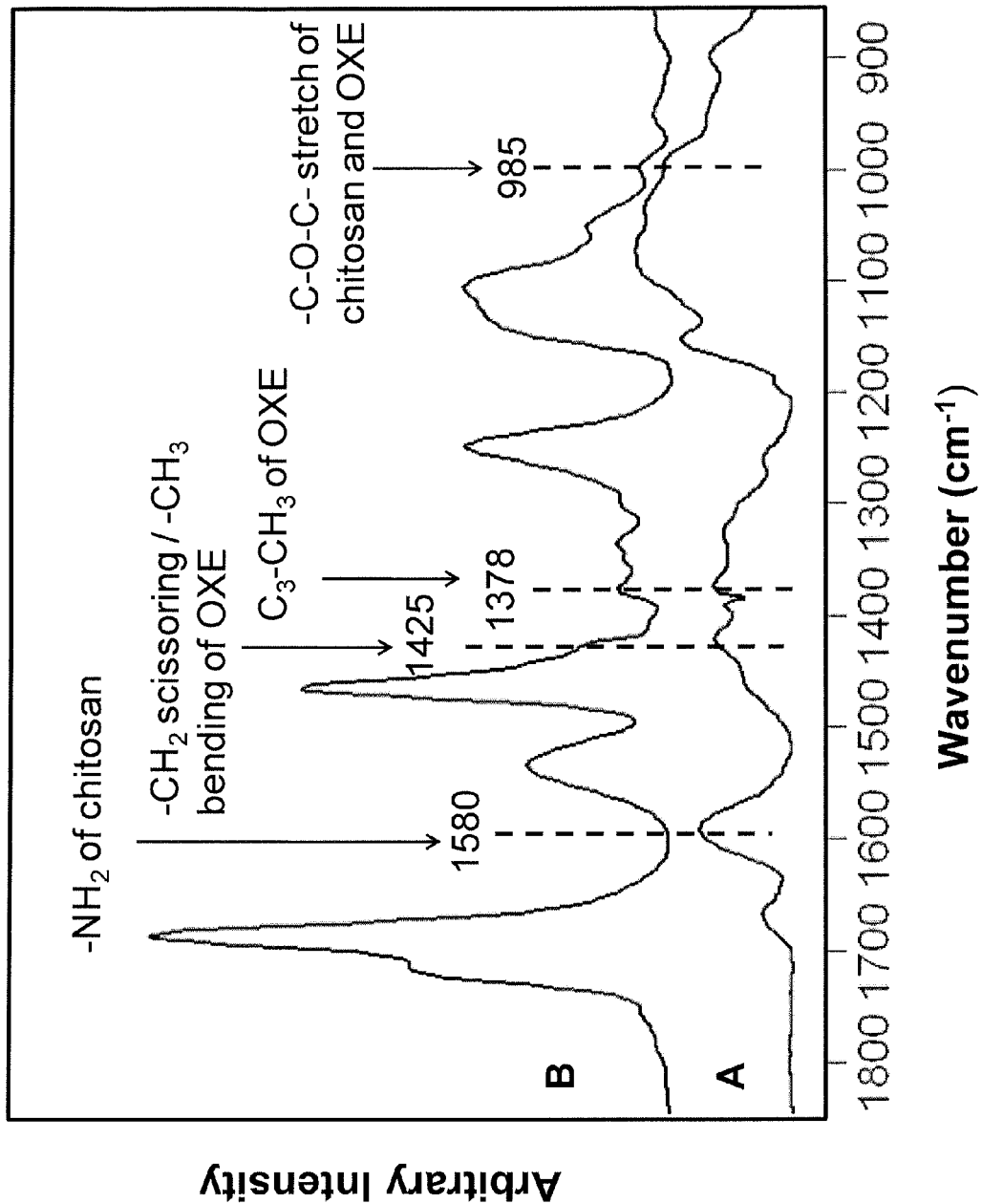
FIG. 9 illustrates an ATR FT-IR spectra of (A) OXE-CHI products and (B) OXE-CHI-PUR networks in accordance with embodiments (wherein OXE is oxetane) of the present invention.
Figure 10:
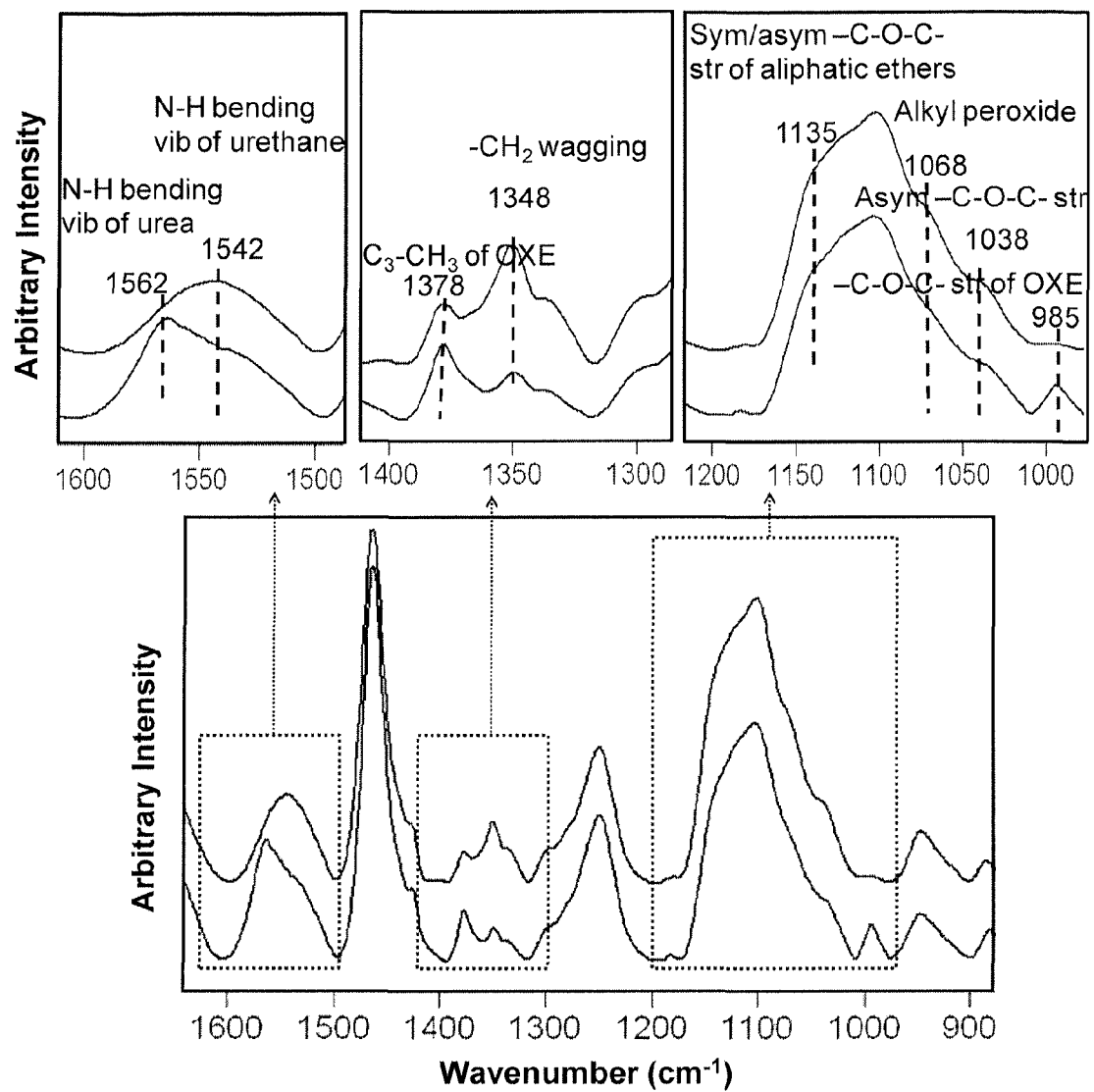
FIG. 10 illustrates an ATR FT-IR spectra of OXE-CHI-PUR networks recorded before (Trace A) and after (Trace B) UV exposure for 30 min of the specimen shown in FIG. 3(A) in accordance with embodiments (wherein OXE is oxetane) of the present invention.

While a cut is a local event at micrometer or smaller scales, the actual cleavage is a molecular level event. To determine the mechanism of repair and to follow molecular events in the damaged area, we utilized localized micro-Attenuated Total Reflectance (μATR) FT-IR spectroscopy and internal reflection IR imaging (IRIRI). As shown in FIGS. 9 and 10, it is believed that the loss of urea and ether linkages of CHI (which is circled in FIG. 1) containing OXE rings results from the UV light exposure of damaged surface areas are responsible for repairing. In these experiments, the repair process utilizes UV light to recombine free radicals to form crosslinks. In the 280-400 nm range, a fluorescent UV lamp generates approximately 0.3 W/m$^2$ per nm power density, whereas the sun gives off about 0.25 W/m$^2$ per nm. Thus, the time frame for repair based upon the sun exposure is very similar when compared to using a fluorescent UV lamp, although the energy density changes as a function of the wavelength of radiation for both sources vary somewhat. Due to stronger sun radiation during summer months in the southern U.S. the repair process will be approximately 3-4 times faster compared to the equivalent exposure in the northern U.S., but for winter months this difference will be negligible. Since crosslinking reactions are not moisture sensitive, dry or humid climate conditions will not affect the repair process. The above networks exhibit the ability to self-repair upon exposure to UV light, but if exactly the same previously repaired spot is damaged again, due to thermosetting characteristics of these networks the ability for further repair may be limited.

As an advantage of the present invention, the use of the UV portion of the electromagnetic radiation from the sun for repairing mechanical damages in coatings offers an ambient temperature approach to self-healing, which is important in a number of applications and technologies that do not require the placement of other often elaborate network components. As another advantage, the self-healing mechanism used in the present invention can be controlled by the chemistries and morphologies of polymer networks produced.

EXAMPLES

Example 1

Materials and Methods

Chitosan (CHI) with a degree of deacetylation ranging from about 75% to about 85%, isopropyl alcohol, methanol, polyethylene glycol (PEG) ($M_w$=300), sodium hydroxide beads, acetone, dimethyl sulfoxide (DMSO), and dibutyltin dilaurate (DBTL) were purchased from Sigma Aldrich Co. 3-(Chloromethyl)-3-methyloxetane and trifunctional homopolymer of hexamethylene diisocyanate (HDI) (Desmodur XP 2410) were obtained from TCI America and Bayer Materials Science.

2 grams of low molecular weight CHI ($M_n$~5×10$^5$) was added into a 150 g 1(N) NaOH solution in a three-neck flask and stirred for 24 hrs at −5° C., followed by refrigeration at −18° C. for 48 hrs. The solution was thawed and mixed with pre-cooled isopropyl alcohol and stirred for 1 hr. 0.06 mole of pre-cooled 3-chloro-3-methyl oxetane was added to the mixture, the temperature was raised to 80° C. and the solution was stirred for 12 hr. The product was filtered and washed several times with methanol until it became neutral, followed by drying it at 60° C. for 12 hr and characterizing it by NMR and IR spectroscopy. The resulting product was identified as oxetane-substituted chitosan (OXE-CHI).

The OXE-CHI product was dispersed in DMSO by sonicating at 25° C. for 12 hrs followed by continuous stirring at 80° C. for 48 hrs. OXE-CHI-PUR films were prepared by reacting trifunctional HDI with dispersed OXE-CHI and polyethylene glycol (PEG) using overhead agitation at 500 rpm with a small four-blade polytetrafluoroethylene (PTFE) impeller in a 50 ml three-neck reaction flask at 25° C. for 10 min under $N_2$ atmosphere. A series of PUR networks were prepared by adjusting the stoichiometric ratios of NCO, OH, and $NH_2$ reactive groups. The following molar ratios of HDI/PEG/CHI and HDI/PEG/OXE-CHI (where HDI/PEG forms PUR) were utilized: HDI/PEG/CHI=1:1.5:0 and 1:1.4:0.57× 10$^4$; HDI/PEG/OXE-CHI=1:1.4:0.57×10$^4$ and 1:1.33:1.17× 10$^4$, respectively, while maintaining 38% (w/w) solids. Such mixtures were applied to obtain an approx. film thickness of 300 pm (±4 μm) on a PTFE substrate at 30° C. under 15% relative humidity (RH) for 12 hrs and in a vacuum oven at 80° C. for 48 hrs. The films were mechanically scratched with a razor blade to obtain a desired width and depth of the scratch. Exposure to UV radiation was conducted using a 120 W fluorescent UV lamp of 302 nm wavelength of light.

Microscopic micro attenuated total reflectance Fourier transform infrared (μATR FT-IR) were obtained using a Bio-Rad FTS-6000 FTIR single-beam spectrometer setting at 4 cm$^{-1}$ resolution. A 2 mm Ge crystal, with a 45° face angle maintaining constant contact pressure between crystal and the film specimens was used. All spectra were corrected for spectral distortions and optical effects using Urban-Huang algorithm (as described in M. W. Urban, *Attenuated Total Reflectance Spectroscopy of Polymers; Theory and Applications* (American Chemical Society and Oxford University Press, Washington, D.C., 1996)). Chitosan powders were analyzed by diffuse reflectance Fourier transfer infrared (DRIFT). In a typical experiment 100 scans were collected. Each spectrum of film represents 100 co-added scans ratioed to 100 reference scans collected using an empty attenuated total reflectance (ATR) cell, whereas for DRIFT the number is 500.

Internal reflection infrared (IRIR) images (as described in D. Otts, P. Zhang, M. W. Urban, *Langmuir* 18, 6473 (2002)) were obtained using a Bio-Rad FTS 7000 Stingray system equipped with internal reflection IR imaging (IRIRI) providing 1 micron spatial resolution. This system consists of a Bio-Rad FTS 7000 spectrometer, a Varian 600 UMA microscope, an image IR focal plane array (FPA) image detector, and internal reflection IR imaging. The IR images were collected using the following spectral acquisition parameters: under sampling ratio 2, rapid-scan speed 5 Hz, number of images per step 64, and spectral resolution 4 cm$^{-1}$. In a typical experiment, spectral data set acquisition time was 1 min and image processing was performed using ENVI software (The Environment for Visualizing Images, Research Systems, Inc.) v. 3.5.

Solid-state $^{13}$C NMR measurements were performed on a Varian$^{UNIT}$ YINOVA 400 spectrometer using a standard Chemagnetics 7.5 mm PENCIL-style probe. Samples were loaded into zirconia rotor sleeves, sealed with Teflon caps, and spun at a rate of 4.5 kHz, The standard cross-polarization magic angle spinning (CP/MAS) technique was used with a high-power proton decoupling implemented during data acquisition. The acquisition parameters were as follows: $^1$H 90° pulse widths was 4.0 μs, the cross-polarization contact time was 1 μs, the dead time delay of 3 s between scans was utilized.

Step 1: Formation of OXE-CHI Precursor

FIGS. 4, 5, and 6 illustrate ATR FT-IR, Raman, and solid state $^{13}$C NMR spectra of OXE-CHI product. FIG. 4, Traces A and B, illustrate ATR-FT-IR spectra of CHI and OXE-CHI, respectively. The bands at 1665 cm$^{-1}$ (—C=O of —NH—CO—CH$_3$) decreases, whereas the band at 1580 cm$^{-1}$ (—NH$_2$, amide I) increases due to the conversion of acetalamide into amide groups (Step 1). Comparison of the band intensities due to CHI (Trace A) and OXE-CHI (Trace B) shows the broadening of the 1070 cm$^{-1}$ band as a result of the overlap of symmetric —C—O—C— stretching vibrations of OXE ring at 1040 cm$^{-1}$ with the —C—O—C— modes of CHI. The symmetric —C—O—C— stretching band at 985 cm$^{-1}$ also increases with respect to the 1070 cm$^{-1}$ band.

Confirmation of the OXE ring incorporation into the CHI backbone is illustrated in Raman spectra shown in FIG. 5. While Trace A illustrates the reference spectrum of CHI, Trace B shows an increase of symmetric —CH2— stretching band of —OCH$_2$— of chitosan at 2885 cm$^{-1}$ due to symmetric and asymmetric stretching of —CH$_3$ group of OXE. The presence of the quaternary ($CC_4$) carbon in the OXE ring and breathing of the ring, which is forbidden in IR, contributes to the enhanced intensity of the band shown in Trace B. The appearance of new bands at 1420 and 1256 cm$^{-1}$ also shows —CH$_2$— scissoring and —CH$_2$ breathing modes of OXE ring, respectively.

Solid-state $^{13}$C NMR spectra are shown in FIG. 6. Trace A shows the $^{13}$C NMR spectrum of CHI and the characteristics resonances due to carbonyl carbon (a) of acetamide group in pyranose ring and carbon (b) attributed to the methyl of acetamide group at 175 and 22.5 ppm are detected, respectively. These resonances are not detected in Trace B due to the conversion of acetamide into primary amine groups and give rise to a new resonances at 23.7 and 40.5 ppm which correspond to carbon atom (d) of the dangling —$CH_3$ group and —$CC_4$ (e) of OXE ring. In Trace A, the resonance at 33.5 ppm corresponds to carbon (c) of the pyranose ring which shifts to 49.8 ppm (Trace B) due to OXE substitution, as shown in FIGS. 6 and 7).

Step 2: Formation of OXE-CHI-PUR Networks.

For reference purposes, FIG. 7 illustrates $^{13}$C NMR spectrum of PUR with characteristic $CH_2$ and C=O resonances. Upon incorporation of OXE-CHI in PUR characteristic resonances at 103 and 85 ppm due to the CHI ring and shift of the 13 ppm resonance due to methyl groups on the OXE ring signify the formation of OXE-CHI-PUR networks, which is illustrated in FIG. 5. Furthermore, ATR FT-IR spectra illustrated in FIG. 9 illustrates the disappearance of the —$NH_2$ bands at 1585 $cm^{-1}$ of the product and detections of new bands at 1425 and 985 $cm^{-1}$ due to CH2 scissoring and —C—O—C— stretching vibration of OXE, respectively, thus confirming the formation of OXE-CHI-PUR networks.

Self-Repairing Mechanism

FIG. 10 illustrates ATR FT-IR spectra recorded before (Trace A) and after the UV exposure (Trace B) of the damaged area of the OXE-CHI-PUR network. The NH— bending vibrations due to polyurea, which is a part of the PUR network at 1562 $cm^{-1}$ (Trace A), shift to 1542 $cm^{-1}$ (Trace B). The latter corresponds to the NH-bending vibrations of the urethane functionality (as described in D. B. Otts, M. W. Urban, *Polymer* 46, 2699 (2005); W. H. Nosal, D. W. Thompson, L. Yan, S. Sarkar, A. Subramanian, J. A. Woollam, *Colloids Surf B* 43, 131 (2005); and K. Heung, M. W. Urban, *Langmuir* 16, 5382 (2000)). These observations indicate a conversion of polyurea to polyurethane linkages. The decrease of the band intensity of the band due to tertiary methyl groups at 1378 $cm^{-1}$ and a subsequent increase of the band due to —$CH_2$ wagging vibrations at 1348 $cm^{-1}$ along with the disappearance of —C—O—C— stretching of OXE at 985 $cm^{-1}$ result from the loss of the OXE ring structure and formation of linear alkyl groups within the network. In contrast, the increase of the band intensities at 1135 and 1068 $cm^{-1}$ due to the —C—O—C— stretching vibrations and alkyl peroxide formation results from the scission of CHI linkages and the OXE ring opening during UV exposure, as described in D. Lin-Vein, N. B. Colthup, W. G. Fateley, J. G. Grasselli, *The Handbook of Infrared and Raman Characteristics Frequencies of Organic Molecules* (Academic Press, San Diego, Calif., 1991); G. Socrates, *Infrared and Raman Characteristic Group Frequencies: Tables and Charts*, 3$^{rd}$ ed. (John Wiley and Sons Ltd., New York, 2001); A. Pawlak, M. Mucha, *Thermochim. Acta* 396, 153 (2003); and E. Pretsch, P. Buhlmann, C. Affolter, *Structure Determination of Organic Compounds*, 3rd ed. (Springer, Germany, 2000).

Figure 11:
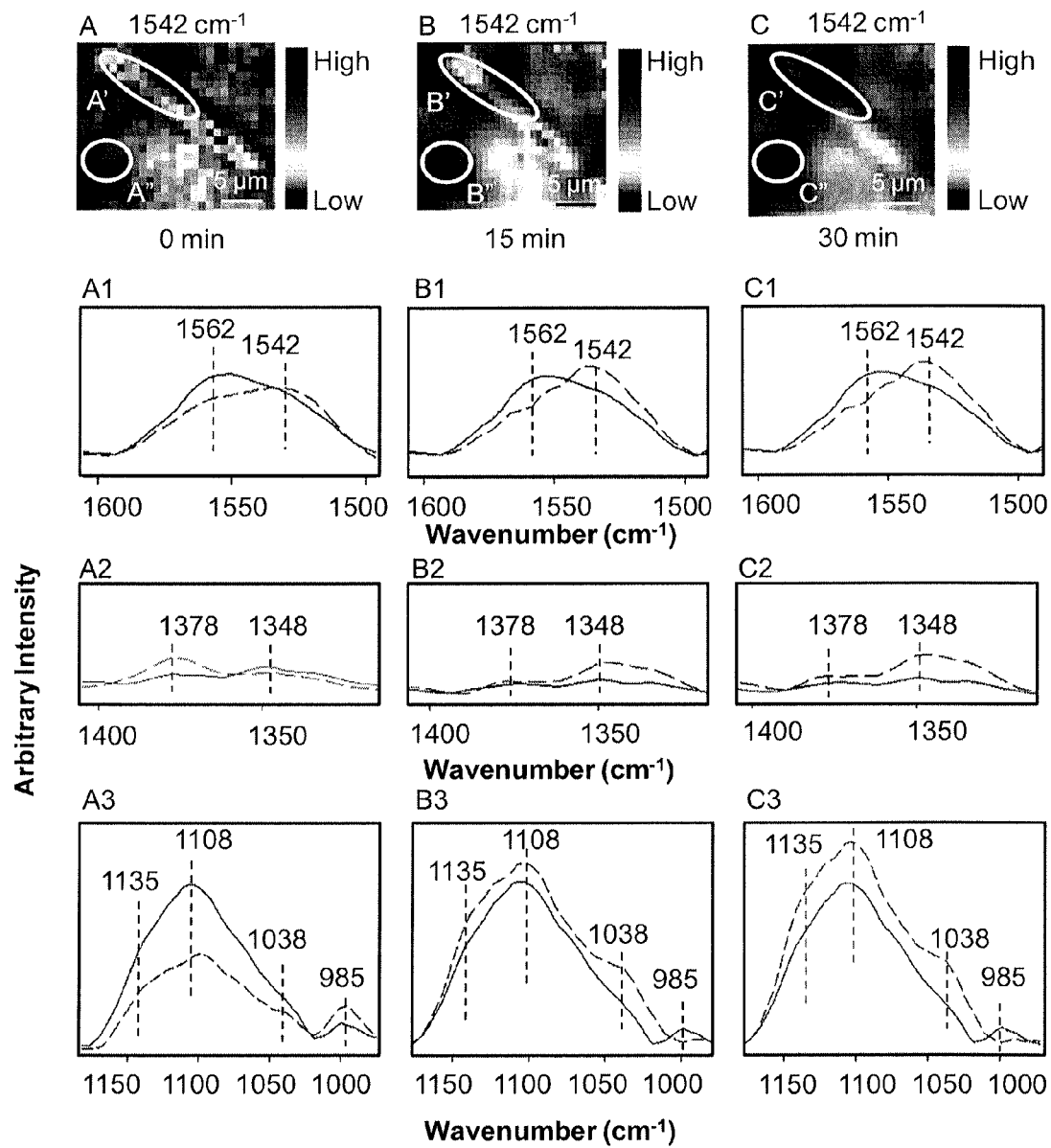
FIG. 11 illustrates internal reflection IR images (IRIRI) recorded from mechanically damaged and undamaged areas of polyurethane network: (A-C) images that were obtained by tuning into the 1542 cm$^{-1}$ band; (A1-A3, B1-B3, C1-C3) IR spectra recorded from mechanically damaged and undamaged areas of (A-C) images, respectively in accordance with embodiments (wherein OXE is oxetane) of the present invention.
Figure 12:
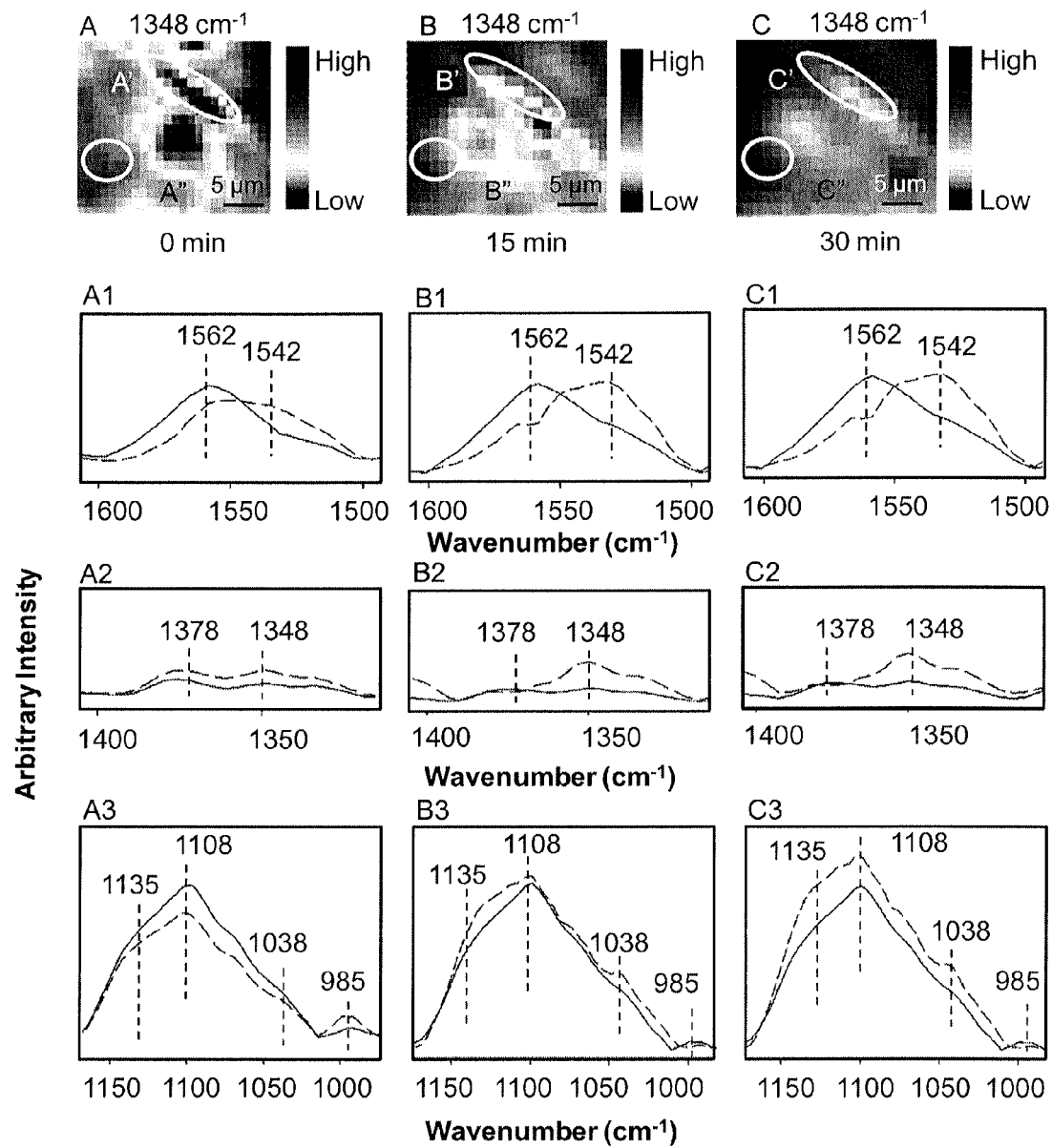
FIG. 12 illustrates internal reflection IR images (IRIRI) recorded from mechanically damaged and undamaged areas of polyurethane network: (A-C) images obtained by tuning into the 1348 cm$^{-1}$ band; (A1-A3, B1-B3, C1-C3) IR spectra recorded from mechanically damaged and undamaged areas of (A-C) images, respectively in accordance with embodiments (wherein OXE is oxetane) of the present invention.

Internal reflection IR imaging was used, as described in D. Otts, P. Zhang, M. W. Urban, *Langmuir* 18, 6473 (2002), which allows users to tune into specific IR bands associated with a given species in a specific damaged area. A spatial resolution is approximately 1 μm. Of particular interest is to determine distribution of the OXE-CHI entities within the networks and to follow molecular events responsible for the network repair. Therefore, the 1542 and 1348 $cm^{-1}$ bands were tuned in due to N—H bending of PUR and $CH_2$ wagging of ether linkages of the OXE ring as a function the UV exposure time. Images A, B, and C in FIGS. 11 and 12 represent distribution of these species in the specific areas labeled A'/A", B'/B", and C'/C" as a function of time, whereas spectral changes recorded from these areas in the 1600-1500 $cm^{-1}$, 1400-1250 $cm^{-1}$, and 1175-975 $cm^{-1}$ are shown in A1, B1, and C1, and are labeled A'/A", B'/B", and C'/C". These spectra represent band intensity changes of species participating in the repair process.

As shown in FIGS. 11, A, B, and C represent three images recorded after UV exposure of OXE-CHI-PUR specimens for 0, 15, and 30 min, respectively. These images were collected from the damaged area shown in FIG. 2 and FIG. 11, A, and exhibits heterogeneous distributions of the 1542 $cm^{-1}$ band. The damaged area labeled A' shows lower concentration levels of the N—H entities, whereas the area A" away from the damage area exhibits higher concentration of these species. The corresponding spectra shown in FIG. 11, A1 obtained from the areas A' and A" confirm that the band intensities of the following vibrations change: decrease of 1562 and 1378 $cm^{-1}$ bands of the urea linkages and —$CH_2$— wagging of linear alkyls, respectively, increase of 1108 $cm^{-1}$ band of —C—O—C— stretching vibrations of linear aliphatic ethers and a decrease of the 985 $cm^{-1}$ band due to —C—O—C— stretching of the OXE ring.

The images recorded from the specimens exposed to UV radiation for 15 and 30 min are shown in FIG. 11, B and C, respectively. The distribution of chemical entities in areas B' and C' appear homogenous, indicating that the surface repair occurred. This is also reflected in spectroscopic changes illustrated in FIG. 11, B1-B3 and C1-C3. As the scratch is exposed to UV, the urea linkage represented by the band at 1562 $cm^{-1}$ shifts to 1542 $cm^{-1}$ which is due to polyurea-polyurethane conversion, whereas the opening of the OXE ring results in the decrease of the band intensities at 1378 and 985 $cm^{-1}$. Increase of the band intensities at 1348, 1135, 1108, and 1038 $cm^{-1}$ in the areas B' and C' corresponds to the —C—O—C— bond formation within the network that is responsible for self-repairing. Similar analysis shown in FIG. 12 was performed by tuning into the 1348 $cm^{-1}$ band due to —$CH_2$— wagging vibrations and showed similar intensity changes of the 1562, 1542, 1135, 1108, 1038 and 985 $cm^{-1}$ bands.

Figure 13:
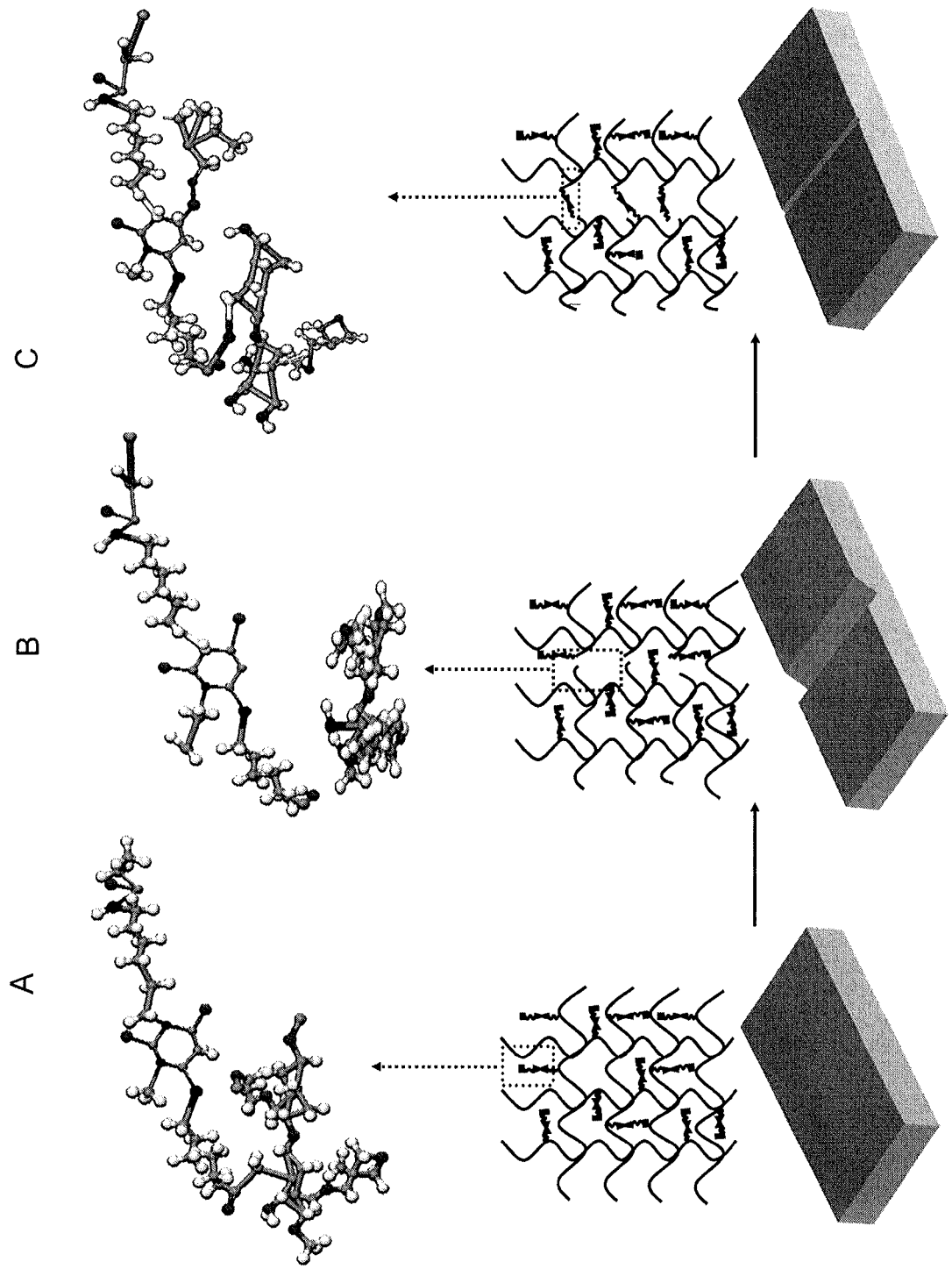
FIG. 13A is a graphical illustration showing mechanical damage of a film (A→B) followed by repair (B→C) and FIG. 13B shows possible chemical reactions leading to repair of OXE-CHI-PUR networks in accordance with embodiments (wherein OXE is oxetane) of the present invention.
Figure 13:
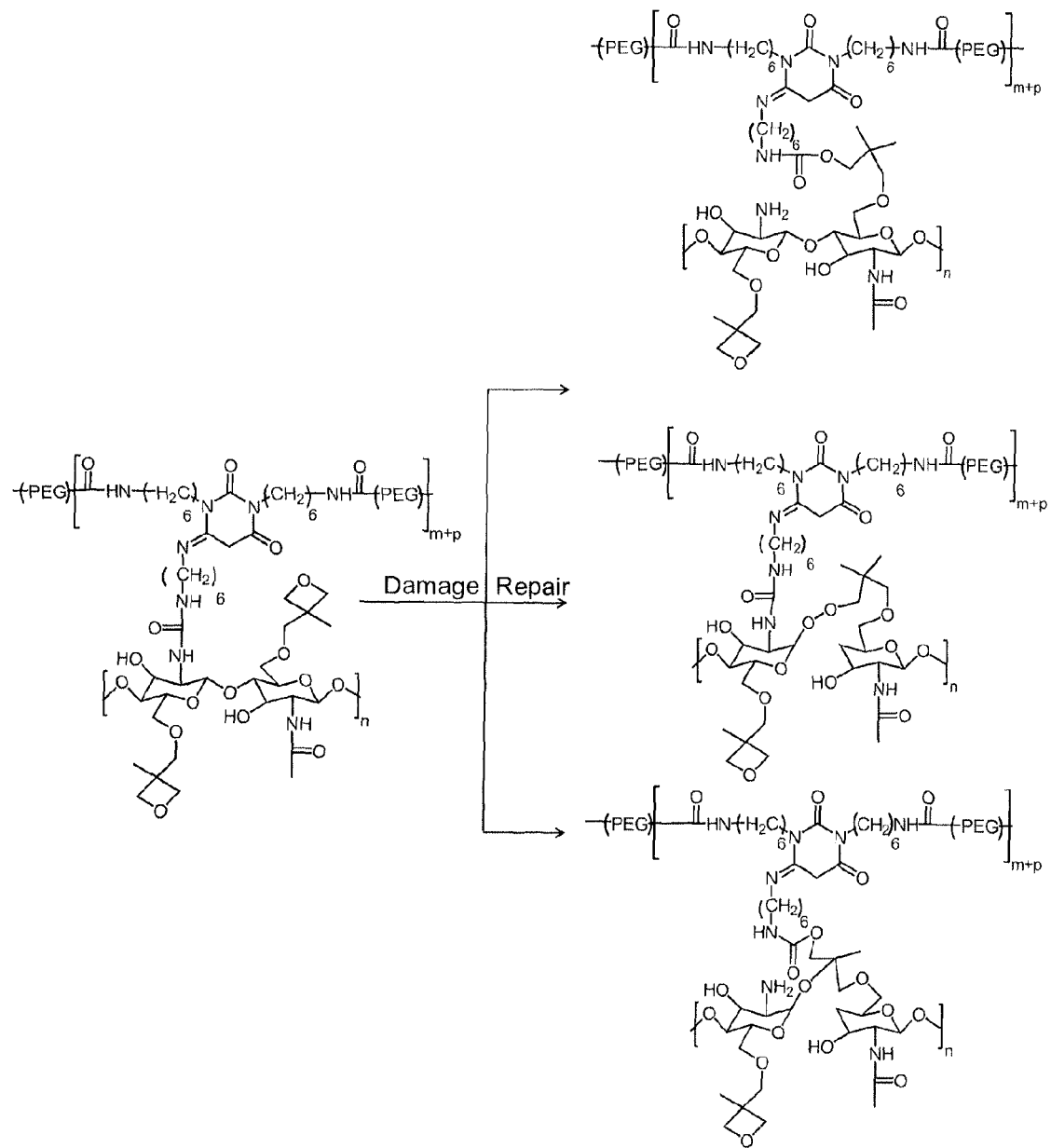

Based on the spectroscopic data analyses, the mechanism of remending of the OXE-CHI-PUR networks is proposed as illustrated in FIG. 13. The crosslinked network is represented by red thick lines, whereas dangling OXE entities are black thinner lines. Molecular segments of OXE-CHI-PUR network responsible for self-healing are also depicted. As a mechanical damage is created, such as shown in FIG. 13, B, OXE rings open up. Upon exposure to UV light, crosslinking reactions of the OXE-CHI entities result in self-healing of the damage area. This is illustrated in FIG. 13, C. Chemical reactions leading to UV-induced repair are also illustrated in FIG. 13. The analysis of the internal reflection IR imaging data (FIGS. 11 and 12) show the decrease of the 1562 and 985 $cm^{-1}$ bands due to urea and the —C—O—C— of oxetane, respectively, and the increase of the 1542, 1135 and 1068 $cm^{-1}$ bands due to urethane, linear —C—O—C— entities, and alkyl peroxides, respectively. These changes allow for the identification of three different products top, middle, and bottom shown in FIG. 13B. FIG. 13B top results from breaking of urea linkages as well as the ring opening of OXE, and formation of urethane linkages, whereas FIG. 13B middle is the product of OXE ring opening and scission of the CHI linkages as a result of an easy cleavage under UV exposure, and the formation of alkyl peroxide linkages. FIG. 13B bottom is the product the urea breakage, CHI and OXE ring opening and formation of urethane and linear —C—O—C crosslinks.

Example 2

Tri-functional homopolymer of hexamethylene diisocyanate (HDI) (Desmodur XP 2410) was obtained from Bayer Material Science. 3-chloro-3-methyl oxetane (OXE) and Tetrahydro-furfuryl chloride (OXO) were purchased from TCI America. Chitosan (CHI) (degree of deacetylation 75-85%), methanol, polyethylene glycol ($M_v$=300), sodium hydroxide beads, acetone, dibutyltin dilaurate (DBTL), dimethyl sulfoxide (DMSO), were purchased from Sigma Aldrich Co.

OXO-substituted chitosan was synthesized by following the previously described procedure. Similarly OXE-OXO-CHI was prepared by reacting equimolar amount of pre-cooled 3-chloro-3-methyl oxetane (OXE) and tetrahydro-furfuryl chloride (OXO) with CHI in alkaline medium.

At first OXO-CHI product was dispersed in DMSO by sonicating at 25° C. for 12 hrs followed by continuous stirring at 80° C. for 48 hrs. Then trifunctional HDI was mixed with dispersed OXE-CHI and PEG using overhead agitation at 500 rpm with a small four-blade polytetrafluoroethylene (PTFE) impeller in a 50 ml three-neck reaction flask at 25° C. for 10 min under nitrogen atmosphere. A series of polyurethane network were made and the relative molar equivalent ratios of isocyanate, PEG and OXO-CHI were varied from 1:1.5:0 to 1:1.33:1.17×10$^{-4}$, while maintaining 38% (w/w) solids in each case. Following the mixing process, such mixture was applied to obtain approx. 300 μm (1 4 pm) thick films on a PTFE substrate at 30° C. under 15% relative humidity (RH) for 12 hrs in a vacuum oven followed by 80° C. for 48 hrs. The films were mechanically damaged with a razor blade to obtain a desired width and depth of the mechanical damage. UV exposures of the films were conducted using a 120 W UV lamp of 302 nm wavelength of light.

Attenuated total reflectance Fourier transform infrared (μATR FT-IR) spectrum were obtained using a Bio-Rad FTS-6000 FTIR single-beam spectrometer setting at 4 cm$^{-1}$ resolution. A 2 mm Ge crystal, with a 45° face angle maintaining constant contact pressure between crystal and the film specimens was used. All IR spectra were corrected for spectral distortions and optical effects using Urban-Huang algorithm. OXO-CHI, OXE-OXO-CHI powders were analyzed by diffuse reflectance Fourier transfer infrared (DRIFT). In a typical experiment 100 scans were collected. Each spectrum of film represents 100 co-added scans ratioed to 100 reference scans collected using an empty attenuated total reflectance (ATR) cell, whereas for DRIFT the number is 500.

Figure 14:
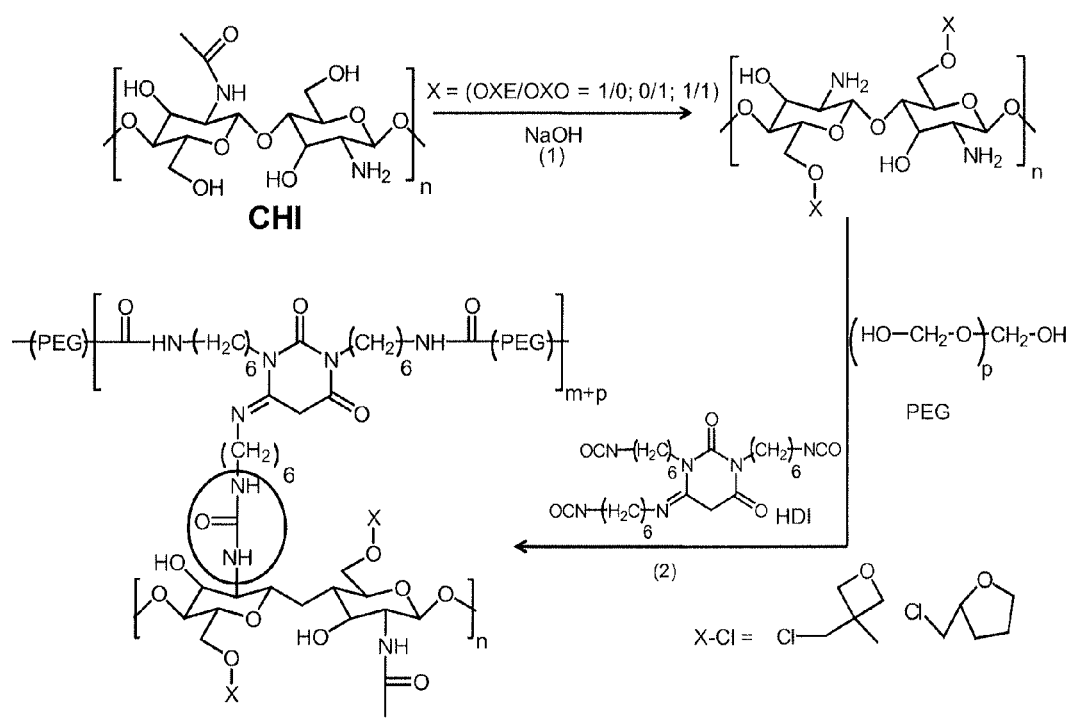
FIG. 14 shows the steps leading to the formation of OXE-CHI-PUR, OXO-CHI-PUR and OXE/OXO-CHI-PUR networks (wherein OXE is oxetane and OXO is oxolane)

FIG. 14 illustrates chemical reactions that lead to the formation of PUR networks containing four (OXE-CHI-PUR), five (OXO-CHI-PUR) member rings, and their combination OXE/OXO-CHI-PUR). The same synthetic protocol was followed as discussed above in Example 1. To verify the formation of OXE-CHI, OXO-CHI, and OXE/OXO-CHI, ATR FT-IR spectra were recorded (not shown herein) Traces, A, B, and C are the spectrum of OXE-CHI, OXO-CHI, and OXE/OXO-CHI-PUR, respectively. For reference, Trace D is the spectra of CHI. As seen in Traces A, B, and C an increase of the intensity of the 1590 cm$^{-1}$ band due to amino groups (amide I) and a decrease of acetamide band (—C=O of —NH—CO—CH$_3$) at 1665 cm$^{-1}$ result from the conversion of acetamide to amide groups. The appearance of new band at 985 cm$^{-1}$ due to symmetric —C—O—C— stretching of OXE (Trace A) indicates the incorporation of OXE within CHI backbone. Trace B illustrates the IR spectrum of OXO-CHI, where the characteristic —C—O—C— stretching band at 1085 cm$^{-1}$ of OXO overlaps with the —C—O—C— stretching band of CHI (Trace D) resulting in increase and the shift of the —C—O—C— band (Trace B). Furthermore, enhanced intensity of the band at 1326 cm$^{-1}$ due to —CH$_2$— deformation modes of OXO is observed in Trace B. On the other hand, Trace C, which illustrates IR spectrum of OXE/OXO-CHI, shows the appearance of new band at 985 cm$^{-1}$ attributed to symmetric —C—O—C— stretching vibrations of OXE ring. Again, the incorporation of OXE in OXE-OXO-CHI is manifested by increase and shift of the 1378 cm$^{-1}$ band attributed to quaternary (CC$_4$) carbon of OXE (Traces A and C). The second step shown in FIG. 1 illustrates reactions leading to the formation of OXE-CHI-PUR, OXO-CHI-PUR, and OXE-OXO-CHI-PUR by the incorporation of HDI in the presence of PEG. As evident in the IR spectra (not shown herein) of Traces A, B and C, the 1562 cm$^{-1}$ band is due to urea linkages, indicating the reaction of substituted chitosans with trifunctional HDI (circled in FIG. 1). Comparison of the band intensities in Traces A, B, and C shows the increase of the 1105 cm$^{-1}$ band due to —C—O—C— stretching vibrations of CHI, while the new 990 cm$^{-1}$ band attributed to symmetric C—O—C— stretching vibrations of OXE is detected in Traces A and C. Furthermore, enhanced intensity of the band at 1326 cm$^{-1}$ due to —CH$_2$-deformation modes of OXO is observed in Traces B and C. In Traces A and C the enhanced intensity of bands at 1378 and 1348 cm$^{-1}$ due to —CC$_4$ of OXE and —CH2- wagging manifest the presence of OXE within the OXE-CHI-PUR and OXE-OXO-CHI-PUR networks, whereas the appearance of 1045 cm$^{-1}$ due to —C—O—C— stretching of OXE in Traces B and C confirms the presence of OXO within OXO-CHI-PUR and OXE-OXO-CHI-PUR networks.

Figure 15:
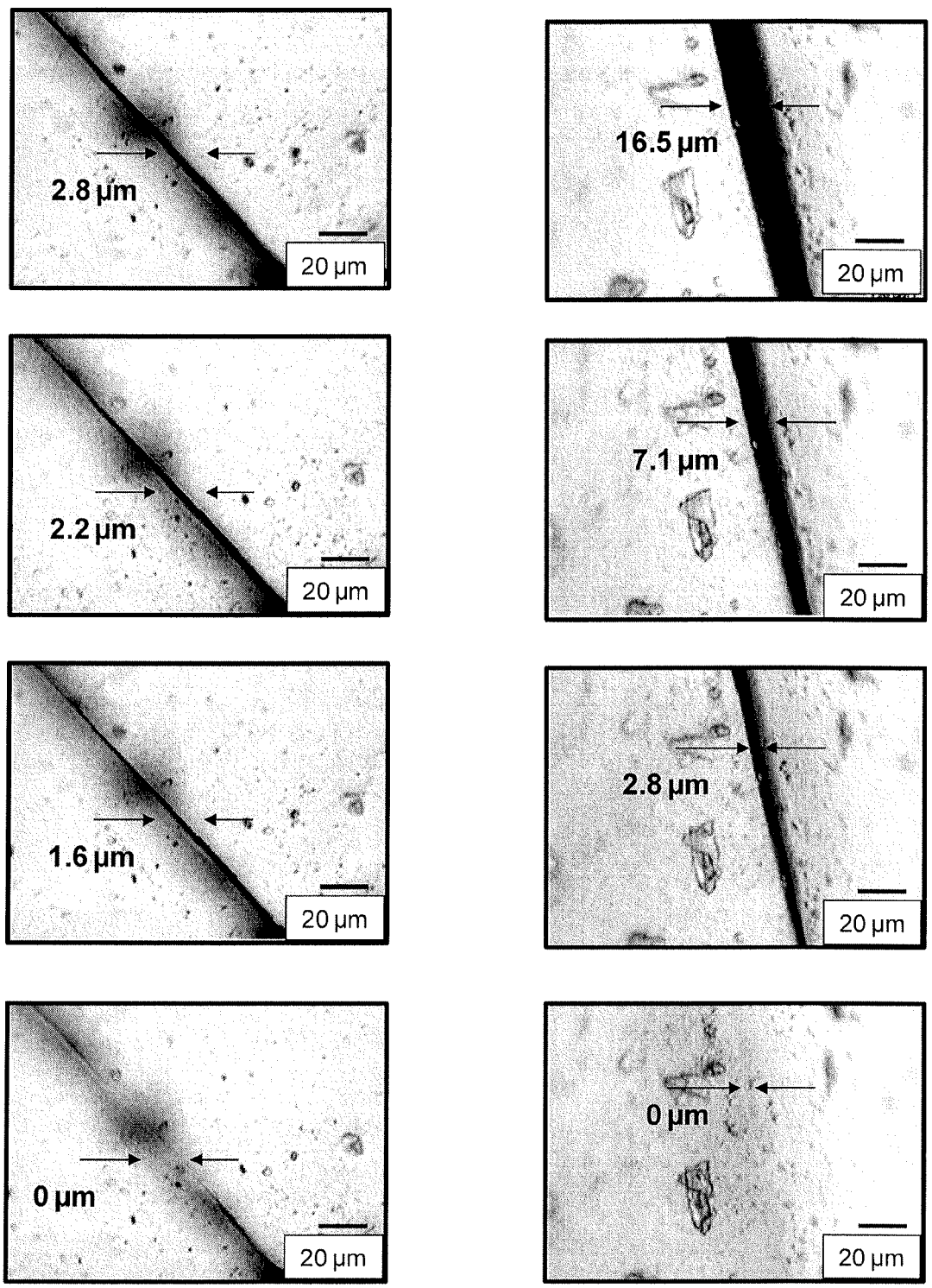
FIG. 15 shows the optical images of OXO-CHI-PUR network recorded as a UV exposure time A1) 0 min; A2) 15 min; A3) 30 min; A4) 60 min and of OXE-OXO-CHI-PUR network B1) 0 min; B2) 15 min; B3) 30 min; B4) 60 min.

When mechanical damage was induced in OXO-CHI-PUR (Panel A) and OXE-OXO-CHI-PUR (Panel B) films, upon exposure to UV light damages disappeared. The sequence of events recorded every 15 min from the time damage was made is shown in FIG. 15, (A1-A4) and (B1-B4). As we recall the repair time for OXE-CHI-PUR for the same stoichiometry the repair time is approximately 30 min. Comparison of these data indicates that the presence of OXO compounds slow down the self-healing ability of the network.

While the invention has been shown or described in only some of its forms, it should be apparent to those skilled in the art that it is not so limited, but is susceptible to various changes without departing from the scope of the invention.

What is claimed is:

1. A cyclic oxide-substituted biodegradable natural polysaccharide polyurethane composition comprising a reaction product of: a) a polyol or a thiol; b) an isocyanate; and c) a composition comprising:

[BNP-OXE$_{1-2}$]$_n$ wherein BNP is a disaccharide of a biodegradable natural polysaccharide selected from the group consisting of chitosan, pectin, heparin, and combinations thereof, OXE is an oxetane, oxolane, or oxepane compound, and n ranges from 5 to about 1475.

2. The composition of claim 1, wherein the isocyanate comprises methylenediisocyanate (MDI); hexamethylenediisocyanate (HDI); isophorenediisocyanate (IPDI); toluenediisocyanate (TDI); 2,4-toluene diisocyanate; 2,6-toluene diisocyanate; 2,2'-methylenediphenylene diisocyanate; 2,4'-methylenediphenylene diisocyanate; 4,4'-methylenediphenylene diisocyanate; polyphenylene polymethylene polyisocyanate; saturated 2,4-methylcyclohexane diisocyanate, saturated 2,6-methylcyclohexane diisocyanate; 2,2'-methylene dicyclohexylene diisocyanate; 2,4'-methylene dicyclohexylene diisocyanate; 4,4'-methylene dicyclohexylene diisocyanate; isophorone diisocyanate; 1,4-diisocyanatobutane; 1,5-diisocyanatopentane; 1,6-diisocyanatohexane; 1,4-cyclohexane diisocyanate; isomeric mixtures thereof; or combinations thereof.

3. The composition of claim 1, wherein the polyol comprises ethylene glycol, diethylene glycol, triethylene glycol, tetraethylene glycol, polyethylene glycol, propylene glycol, dipropylene glycol, polypropylene glycol, 1,4-butanediol, 1,6-hexanediol, polytetramethylene glycol, polyesterdiol, derivatives thereof, or combinations thereof.

4. The composition of claim 1, wherein the thiol comprises polythiol, pentaerythritol tetrakis(3-mercaptoproprionate) (PET3MP), trifunctional thiols, tetrafunctional thiols, thiol esters, thiol acrylates, or combinations thereof.

5. A cyclic oxide-substituted chitosan composition comprising:

[CHI-OXE$_{1-2}$]$_n$ wherein CHI is a disaccharide of chitosan, OXE is an oxolane compound, and n ranges from 5 to about 1475.

6. A cyclic oxide-substituted chitosan polyurethane composition comprising a reaction product of a) a polyol or a thiol; b) an isocyanate; and c) a composition comprising:

[CHI-OXE$_{1-2}$]$_n$ wherein CHI is a disaccharide of chitosan, OXE is an oxetane, oxolane or oxepane compound, and n ranges from 5 to about 1475.

7. The composition of claim 6 formed into a coating or a film.

8. The cyclic oxide-substituted chitosan polyurethane composition of claim 6 comprising:

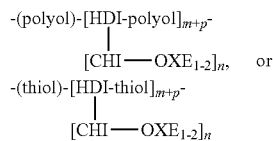

wherein HDI is an isocyanate, CHI is a disaccharide of chitosan, OXE is an oxetane, oxolane or oxepane compound, m ranges from 3-450, p ranges from 0-540, and n ranges from 5 to about 1475.

9. The composition of claim 8, wherein the isocyanate comprises methylenediisocyanate (MDI); hexamethylenediisocyanate (HDI); isophorenediisocyanate (IPDI); toluenediisocyanate (TDI); 2,4-toluene diisocyanate; 2,6-toluene diisocyanate; 2,2'-methylenediphenylene diisocyanate; 2,4'-methylenediphenylene diisocyanate; 4,4'-methylenediphenylene diisocyanate; polyphenylene polymethylene polyisocyanate; saturated 2,4-methylcyclohexane diisocyanate, saturated 2,6-methylcyclohexane diisocyanate; 2,2'-methylene dicyclohexylene diisocyanate; 2,4'-methylene dicyclohexylene diisocyanate; 4,4'-methylene dicyclohexylene diisocyanate; isophorone diisocyanate; 1,4-diisocyanatobutane; 1,5-diisocyanatopentane; 1,6-diisocyanatohexane; 1,4-cyclohexane diisocyanate; isomeric mixtures thereof; or combinations thereof.

10. The composition of claim 8, wherein the polyol comprises ethylene glycol, diethylene glycol, triethylene glycol, tetraethylene glycol, polyethylene glycol, propylene glycol, dipropylene glycol, polypropylene glycol, 1,4-butanediol, 1,6-hexanediol, polytetramethylene glycol, polyesterdiol, derivatives thereof, or combinations thereof.

11. The composition of claim 8, wherein the thiol comprises polythiol, pentaerythritol tetrakis(3-mercaptoproprionate) (PET3MP), trifunctional thiols, tetrafunctional thiols, thiol esters, thiol acrylates, or combinations thereof.

12. The composition of claim 8, wherein the chitosan has a degree of deacetylation ranging from about 75% to about 85%.

13. The composition of claim 8, further comprising an alkaline solvent.

14. The composition of claim 8, wherein OXE is an oxetane compound.

15. The composition of claim 8, wherein OXE is an oxolane compound.

16. A method of prophylactically repairing mechanical damage to a substrate comprising the steps of applying the composition of claim 6 to a substrate, wherein upon exposure of the substrate to a UV source, the composition initiates self-repair of the mechanical damage to the substrate.

17. The method of claim 16, wherein the substrate comprises metal, plastic, glass, or combinations thereof.

* * * * *

UNITED STATES PATENT AND TRADEMARK OFFICE
CERTIFICATE OF CORRECTION

| | |
|---|---|
| PATENT NO. | : 9,200,089 B2 |
| APPLICATION NO. | : 14/152023 |
| DATED | : December 1, 2015 |
| INVENTOR(S) | : Marek W. Urban and Biswajit Ghosh |

It is certified that error appears in the above-identified patent and that said Letters Patent is hereby corrected as shown below:

In the Specification

COLUMN 1

At Lines 20-21, "government may have certain rights in this invention" should read --government has certain rights in the invention--.

Signed and Sealed this
Fourteenth Day of June, 2016

Michelle K. Lee
*Director of the United States Patent and Trademark Office*